(12) United States Patent
Guercio

(10) Patent No.: US 11,702,393 B2
(45) Date of Patent: Jul. 18, 2023

(54) SYNTHESIS OF A MONOACYLGLYCEROL LIPASE INHIBITOR

(71) Applicant: H. LUNDBECK A/S, Valby (DK)

(72) Inventor: Giuseppe Guercio, Padua (IT)

(73) Assignee: H. LUNDBECK A/S, Valby (DK)

( * ) Notice: Subject to any disclaimer, the term of this patent is extended or adjusted under 35 U.S.C. 154(b) by 104 days.

(21) Appl. No.: 17/234,660

(22) Filed: Apr. 19, 2021

(65) Prior Publication Data

US 2021/0323938 A1 Oct. 21, 2021

Related U.S. Application Data

(60) Provisional application No. 63/013,454, filed on Apr. 21, 2020.

(51) Int. Cl.
*C07D 295/02* (2006.01)
*C07D 295/023* (2006.01)

(52) U.S. Cl.
CPC ....... *C07D 295/02* (2013.01); *C07D 295/023* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 4,327,725 A | 5/1982 | Cortese et al. | |
| 4,624,848 A | 11/1986 | Lee | |
| 4,968,509 A | 11/1990 | Radebaugh et al. | |
| 5,323,907 A | 6/1994 | Kalvelage | |
| 5,456,923 A | 10/1995 | Nakamichi et al. | |
| 5,461,140 A | 10/1995 | Heller et al. | |
| 5,516,527 A | 5/1996 | Curatolo | |
| 5,622,721 A | 4/1997 | Dansereau et al. | |
| 5,686,105 A | 11/1997 | Kelm et al. | |
| 5,700,410 A | 12/1997 | Nakamichi et al. | |
| 5,977,175 A | 11/1999 | Lin | |
| 6,465,014 B1 | 10/2002 | Moroni et al. | |
| 6,932,983 B1 | 8/2005 | Straub et al. | |
| 9,133,148 B2 | 9/2015 | Cisar et al. | |
| 9,487,495 B2 | 11/2016 | Cisar et al. | |
| 9,771,341 B2 | 9/2017 | Cisar et al. | |
| 9,957,242 B2 | 5/2018 | Cisar et al. | |
| 9,981,930 B1 | 5/2018 | Grice et al. | |
| 9,994,537 B2 | 6/2018 | Cisar et al. | |
| 10,093,635 B2 | 10/2018 | Grice et al. | |
| 10,450,302 B2 | 10/2019 | Blankman et al. | |
| 10,463,753 B2 | 11/2019 | Grice et al. | |
| 11,021,453 B2 | 6/2021 | Cisar et al. | |
| 11,034,674 B2 | 6/2021 | Blankman et al. | |
| 2008/0214524 A1 | 9/2008 | Lee et al. | |
| 2010/0015225 A1 | 1/2010 | Diederich et al. | |
| 2011/0275650 A1 | 11/2011 | Cravatt et al. | |
| 2014/0163068 A1 | 6/2014 | Verwijs et al. | |
| 2014/0357693 A1 | 12/2014 | Shaul et al. | |
| 2015/0018335 A1 | 1/2015 | Cisar et al. | |
| 2015/0148330 A1 | 5/2015 | Cisar et al. | |
| 2015/0313843 A1 | 11/2015 | Shaw et al. | |
| 2016/0137649 A1 | 5/2016 | Jones et al. | |
| 2016/0272602 A1 | 9/2016 | Cisar et al. | |
| 2018/0099951 A1* | 4/2018 | Blankman | C07D 403/10 |
| 2018/0134674 A1 | 5/2018 | Grice et al. | |
| 2018/0134675 A1* | 5/2018 | Grice | A61P 29/02 |
| 2018/0208568 A1 | 7/2018 | Cisar et al. | |
| 2019/0202801 A1* | 7/2019 | Grice | C07D 487/08 |
| 2020/0190063 A1 | 6/2020 | Grice et al. | |
| 2021/0188793 A1 | 6/2021 | Cisar et al. | |
| 2021/0230145 A1 | 7/2021 | Blankman et al. | |

FOREIGN PATENT DOCUMENTS

| | | |
|---|---|---|
| CN | 104379578 A | 2/2015 |
| DE | 1802739 A1 | 6/1969 |
| JP | S6183073 A | 4/1986 |
| JP | 2000500448 A | 1/2000 |
| JP | 2008500270 A | 1/2008 |
| JP | 2008521768 A | 6/2008 |
| JP | 2009523729 A | 6/2009 |
| JP | 2010513447 A | 4/2010 |
| RU | 2167150 C2 | 5/2001 |
| WO | WO-8911794 A1 | 12/1989 |
| WO | WO-9311097 A1 | 6/1993 |
| WO | WO-9517439 A2 | 6/1995 |
| WO | WO-9800408 A1 | 1/1998 |
| WO | WO-0125188 A1 | 4/2001 |
| WO | WO-0234382 A1 | 5/2002 |
| WO | WO-2005063698 A1 | 7/2005 |
| WO | WO-2005070910 A2 | 8/2005 |
| WO | WO-2005080363 A1 | 9/2005 |
| WO | WO-2006074025 A1 | 7/2006 |
| WO | WO-2008106047 A2 | 9/2008 |

(Continued)

OTHER PUBLICATIONS

Aitipamula et al. Polymorphs, Salts, and Cocrystals: What's in a Name? Cryst. Growth Des. 12:2147-2152 (2012).

Alhouayek et al. Increasing endogenous 2-arachidonoylglycerol levels counteracts colitis and related systemic inflammation. FASEB 25(8):2711-2721 (2011).

Ameloot et al. Endocannabinoid control of gastric sensorimotor function in man. Aliment Pharmacol Ther 31(10):1123-1131 (2010).

Anderson et al. Actions of the dual FAAH/MAGL inhibitor JZL195 in a murine inflammatory pain model. Neuropharmacology 81:224-230 (2013).

Berge et al. Pharmaceutical Salts. Journal of Pharmaceutical Sciences 66(1):1-19 (Jan. 1977).

Bernstein. Crystal Structure Prediction and Polymorphism. ACA Transactions 39:14-23 (2004).

(Continued)

*Primary Examiner* — Medhanit W Bahta

(74) *Attorney, Agent, or Firm* — Wilson Sonsini Goodrich & Rosati

(57) ABSTRACT

Described herein is the manufacture of MAGL inhibitor 1,1,1,3,3,3-hexafluoropropan-2-yl 4-(2-(pyrrolidin-1-yl)-4-(trifluoromethyl)benzyl)piperazine-1-carboxylate including salts thereof.

16 Claims, 2 Drawing Sheets

(56) References Cited

FOREIGN PATENT DOCUMENTS

| WO | WO-2009135915 A1 | 11/2009 | | |
|---|---|---|---|---|
| WO | WO-2009141238 A1 | 11/2009 | | |
| WO | WO-2010009207 A1 | 1/2010 | | |
| WO | WO-2010063802 A1 | 6/2010 | | |
| WO | WO-2010111050 A1 | 9/2010 | | |
| WO | WO-2010129497 A1 | 11/2010 | | |
| WO | WO-2011054795 A1 | 5/2011 | | |
| WO | WO-2011151808 A1 | 12/2011 | | |
| WO | WO-2013102431 A1 | 7/2013 | | |
| WO | WO-2013103973 A1 | 7/2013 | | |
| WO | WO-2013142307 A1 | 9/2013 | | |
| WO | WO-2013159095 A1 | 10/2013 | | |
| WO | WO-2015179559 A2 | 11/2015 | | |
| WO | WO-2016014975 A2 | 1/2016 | | |
| WO | WO-2016149401 A2 | 9/2016 | | |
| WO | WO-2016183097 A1 | 11/2016 | | |
| WO | WO-2018093946 A1 | 5/2018 | | |
| WO | WO-2018093947 A1 | 5/2018 | | |
| WO | WO-2018093949 A1 | 5/2018 | | |
| WO | WO-2018093953 A1 * | 5/2018 | ........... | A61K 31/496 |
| WO | WO-2019046330 A1 | 3/2019 | | |
| WO | WO-2019222266 A1 | 11/2019 | | |
| WO | WO-2021214550 A1 | 10/2021 | | |

OTHER PUBLICATIONS

Blake et al. Preliminary assessment of the efficacy, tolerability and safety of a cannabis-based medicine (Sativex) in the treatment of pain caused by rheumatoid arthritis. Rheumatology (Oxford) 45(1):50-52 (2006).

Blankman et al. A comprehensive profile of brain enzymes that hydrolyze the endocannabinoid 2-arachidonoylglycerol. Chem. Biol. 14:1347-1356 (2007).

Braga et al. Making crystals from crystals: a green route to crystal engineering and polymorphism. Chemical Communications (29):3635-45 (2005).

Burckhardt et al. The fibromyalgia impact questionnaire: development and validation. J Rheumatol 18(5):728-733 (1991).

Chang et al. Highly Selective Inhibitors of Monoacylglycerol Lipase Bearing a Reactive Group that is Bioisosteric with Endocannabinoid Substrates. ChemBiol 19(5):579-588 (2012).

Chang et al. Proteome-wide reactivity profiling identifies diverse carbamate chemotypes tuned for serine hydrolase inhibition. ACS Chem Biol 8:1590-1599 (2013).

Chen et al. Monoacylglycerol lipase is a therapeutic target for Alzheimer's disease. Cell Rep. 2(5):1329-1339 (2012).

Cisar et al. Identification of ABX-1431, a Selective Inhibitor of Monoacylglycerol Lipase 1 and Clinical Candidate for Treatment of Neurological Disorders. J Med Chem 61:9062-9084 (2018).

Collin et al. A double-blind, randomized, placebo-controlled, parallel-group study of Sativex, in subjects with symptoms of spasticity due to multiple sclerosis. Neurol Res 32(5):451-459 (2010).

Collin et al. Randomized controlled trial of cannabis-based medicine in spasticity caused by multiple sclerosis. Eur J Neurol 14(3):290-296 (2007).

Fiz et al. Cannabis use in patients with fibromyalgia: effect on symptoms relief and health-related quality of life. PLoS One 6(4):e18440 (2011).

Fleisher et al. Improved oral drug delivery: solubility limitations overcome by the use of prodrugs. Advanced Drug Delivery Reviews 19:115-130 (1996).

Foster et al. Deuterium isotope effects in the metabolism of drugs and xenobiotics: implications for drug design. Adv Drug Res 14:1-36 (1985).

Fowler. Monoacylglycerol lipase—a target fordrug development? Br Pharmacol. 166:1568-1585 (2012).

Gately et al. Deuterioglucose: alteration of biodistribution by an isotope effect. J Nucl Med 27:388-394 (1986).

Gordon et al. The metabolism of the abortifacient terpene, (R)-(+)-pulegone, to a proximate toxin, menthofuran. Drug Metab Dispos 15:589-594(1987).

Guindon et al. Alterations in endocannabinoid tone following chemotherapy-induced peripheral neuropathy: effects of endocannabinoid deactivation inhibitors targeting fatty-acid amide hydrolase and monoacylglycerol lipase in comparison to reference analgesics following cisplatin treatment. Pharmacol Res 67(1):94-109 (2013).

Guindon et al. Peripheral Antinociceptive Effects of Inhibitors of Monoacylglycerol Lipase in a Rat Model of Inflammatory Pain. Br J Pharmacol 163(7):1464-1478 (2011).

Hanlon et al. Circadian rhythm of circulating levels of the endocannabinoid 2-arachidonoylglycerol. J Clin Endocrinol Metab 100:220-226 (2015).

Hill. Medical Marijuana for Treatment of Chronic Pain and Other Medical and Psychiatric Problems: A Clinical Review. JAMA 313(24):2474-2483 (2015).

Howard et al. Cannabis use in sickle cell disease: a questionnaire study. Br J Haematol 131(1):123-128 (2005).

Hruba et al. Simultaneous Inhibition of Fatty Acid Amide Hydrolase and Monoacylglycerol Lipase Shares Discriminative Stimulus Effects with delta9-Tetarhydrocannabinol in Mice. The Journal of Pharmacology and Experimental Therapeutics 353:261-268 (2015).

Jiang et al. Application of deuteration in drug research. Qilu Pharmaceutical Affairs 29.11 (2010):82-684 (English Abstract).

Jiang et al. (+)-Borneol alleviates mechanical hyperalgesia in models of chronic inflammatory and neuropathic pain in mice. Eur J Pharmacol 757:53-58 (2015).

Jones et al. Pharmaceutical Cocrystals: An Emerging Approach to Physical Property Enhancement. MRS Bulletin 31:875-879 (2006).

Khasabova et al. Increasing 2-arachidonoyl glycerol signaling in the periphery attenuates mechanical hyperalgesia in a model of bone cancer pain. Pharmacol Res 64(1):60-67 (2011).

King et al. URB602 inhibits monoacylglycerol lipase and selectively blocks 2-arachidonoylglycerol degradation in intact brain slices. Chem Biol 14(12):1357-1365 (2007).

Kinsey et al. Blockade of Endocannabinoid-Degrading Enzymes Attenuates Neuropathic Pain. J Pharmacol Exp Ther 330(3):902-910 (2009).

Kohli et al. Pain-related behaviors and neurochemical alterations in mice expressing sickle hemoglobin: modulation by cannabinoids. Blood 116(3):456-465 (2010).

Korhonen et al. Piperazine and piperidine carboxamides and carbamates as inhibitors of fatty acid amide hydrolase (FAAH) and monoacylglycerol lipase (MAGL). Bioorg Med Chem 22(23):6694-6705 (2014).

Kushner et al. Pharmacological uses and perspectives of heavy water and deuterated compounds. Can J Physiol Pharmacol 77:79-88 (1999).

Labar et al. A review on the monoacylglycerol lipase: at the interface between fat and endocannabinoid signalling. Curr Med Chem 17(24):2588-2607 (2010).

Langford et al. A double-blind, randomized, placebo-controlled, parallel-group study of THC/CBD oromucosal spray in combination with the existing treatment regimen, in the relief of central neuropathic pain in patients with multiple sclerosis. J Neurol 260(4):984-997 (2013).

Liberman et al. Pharmaceutical Dosage Forms. 2nd Ed. 1:209-214 (1990).

Lijinsky et al. Dose-response studies in carcinogenesis by nitroso-N-methyl-N-(2-phenyl)ethylamine in rats and the effects of deuterium substitution. Food Chem Toxicol 20:393-399 (1982).

Lijinsky et al. Dose-response studies with nitrosoheptamethyleneimine and its alpha-deuterium-labeled derivative in F344 rats. J Nat Cancer Inst 69:1127-1133 (1982).

Long et al. Characterization of tunable piperidine and piperazine carbamates as inhibitors of endocannabinoid hydrolases. J Med chem 53(4):1830-1842 (2010).

Long et al. Dual blockade of FAAH and MAGL identifies behavioral processes regulated by endocannabinoid crosstalk in vivo. PNAS USA 106(48):20270-20275 (2009).

(56) References Cited

OTHER PUBLICATIONS

Long et al. Selective blockade of 2-arachidonoylglycerol hydrolysis produces cannabinoid behavioral effects. Nat Chem Biol. 5(1):37-44 (2009).
Ly et al. Increased cerebral cannabinoid-1 receptor availability is a stable feature of functional dyspepsia: a [F]MK-9470 PET study. Psychother Psychosom 84(3):149-158 (2015).
Malik et al. Dronabinol increases pain threshold in patients with functional chest pain: a pilot double-blind placebo-controlled trial. Dis Esophagus 30(2):1-8 (2017).
Mangold et al. Effects of deuterium labeling on azido amino acid mutagenicity in Salmonella typhimurium. Mutat Res 308:33-42 (1994).
Meanwell et al. Synopsis of some recent tactical application of bioisosteres in drug design. J Med Chem 54(8):2529-2591 (2011).
Mease et al. A randomized, double-blind, placebo-controlled, phase III trial of pregabalin in the treatment of patients with fibromyalgia. J Rheumatol 35(3):502-514 (2008).
Müller-Vahl et al. Treatment of Tourette's syndrome with Delta 9-tetrahydrocannabinol (THC): a randomized crossover trial. Pharmacopsychiatry 35(2):57-61 (2002).
Mukhamadieva et al. Search For New Drugs Synthesis and Biological Activity of O-Carbamoylated 1,1,1,3,3,3-Hexafluoroisopropanols as New Specific Inhibitors of Carboxylesterase. Pharmaceutical Chemistry Journal 46(8):461-464 (2012).
Muller-Vahl et al. Treatment of Tourette Syndrome with Delta-9-Tetrahydrocannbinol (delta9-THC): No Influence on Neuropsychological Performance. Neuropsychopharmacology 28:384-388 (2003).
Niphakis et al. O-Hydroxyacetamide Carbamates as a Highly Potent and Selective Class of Endocannabinoid Hydrolase Inhibitors. ACS Chem. Neurosci. 3(5):418-426 (2012/Web2011).
Nomura et al. Endocannabinoid hydrolysis generates brain prostaglandins that promote neuroinflammation. Science 334(6057):809-813 (2011).
Patani et al. Bioisosterism: A Rational Approach in Drug Design. Chem. Rev. 96:3147-3176 (1996).
PCT/US2013/020551 International Preliminary Report on Patentability dated Jul. 17, 2014.
PCT/US2013/020551 International Search Report dated May 21, 2013.
PCT/US2016/022690 International Search Report and Written Opinion dated Aug. 30, 2016.
PCT/US2016/031668 International Search Report and Written Opinion dated Aug. 11, 2016.
PCT/US2017/061867 International Search Report and Written Opinion dated Mar. 23, 2018.
PCT/US2017/061867 Invitation to Pay Additional Fees dated Jan. 22, 2018.
PCT/US2017/061868 International Search Report and Written Opinion dated Mar. 20, 2018.
PCT/US2017/061868 Invitation to Pay Additional Fees dated Jan. 22, 2018.
PCT/US2017/061875 International Search Report and Written Opinion dated Feb. 7, 2018.
Pellkofer et al. The major brain endocannabinoid 2-AG controls neuropathic pain and mechanical hyperalgesia in patients with neuromyelitis optical. PLoS One 8(8):e71500 (2013).
Piro et al. A dysregulated endocannabinoid-eicosanoid network supports pathogenesis in a mouse model of Alzheimer's disease. Cell Rep. 1(6):617-623 (2012).
Porsteinsson et al. Effect of citalopram on agitation in Alzheimer disease: the CitAD randomized clinical trial. JAMA 311 (7):682-691 (2014).
Price. The computational prediction of pharmaceutical crystal structures and polymorphism. Advanced Drug Delivery Reviews 56:301-319 (2004).
PubChem CID 17217128 http://pubchem.ncbi.nlm.nih.gov/summary/summary.cgi?cid=17217128 Retrieved Apr. 30, 2013 Create Date: Nov. 13, 2007 (3 pgs.).

PubChem CID 3469875. Compound Summary downloaded at https://pubchem.ncbi.nlm.nih.gov/compound/3469875 on Jun. 5, 2019,pp. 1-8 (2019).
PubChem CID 3469875. http://pubchem.ncbi.nlm.nih.gov/summary/summary.cgi?cid=3469875Retrieved Mar. 4, 2013 Create Date: Sep. 8, 2005 (11 pgs.).
PubChem CID 669902 http://pubchem.ncbi.nlm.nih.gov/summary/summary.cgi?cid=669902 Retrieved May 1, 2013 Create Date: Jul. 8, 2005 (4 pgs.).
PubChem CID 71657619 Create date: Aug. 19, 2013 (12 pgs).
Rautio et al. Prodrugs: design and clinical applications. Nat Rev Drug Discov 7(3):255-270 (2008).
Rhyne et al. Effects of Medical Marijuana on Migraine Headache Frequency in an Adult Population. Pharmacotherapy 36:505-510 (2016).
Richardson et al. Characterisation of the cannabinoid receptor system in synovial tissue and fluid in patients with osteoarthritis and rheumatoid arthritis. Arthritis Res Ther 10(2):R43 (2008).
Rog et al. Randomized, controlled trial of cannabis-based medicine in central pain in multiple sclerosis. Neurology 65(6):812-819 (2005).
Sarchielli et al. Endocannabinoids in chronic migraine: CSF findings suggest a system failure. Neuropsychopharmacology 32(6):1384-1390 (2007).
Science IP Report dated Dec. 11, 2014 (126 pgs.).
Silverman. The Organic Chemistry of Drug Design and Drug Action. Academic Press (pp. 15-22) (1992).
Singh et al. Encyclopedia of Pharmaceutical Technology 2nd Ed. pp. 751-753 (2002).
Skrabek et al. Nabilone for the treatment of pain in fibromyalgia. J Pain 9(2):164-173 (2008).
South. Synthesis and Reactions of Halogenated Thiazole Isocyanates. Journal of Heterocyclic Chemistry 28:1003-1011 (1991).
Studnev et al. Synthesis, Antibacterial and Immunotropic Activity of Poly(fluoroalkyl-N-arylcarbamates. Pharmaceutical Chemistry Journal 36(12):654-657 (2002).
Thornber. Isosterism and molecular modification in drug design. Chem Soc Rev 8:563-580 (1979).
Turcotte et al. Nabilone as an adjunctive to gabapentin for multiple sclerosis-induced neuropathic pain: a randomized controlled trial. Pain Med 16(1):149-159 (2015).
Urry et al. Free-radical chain addition reactions of aldehydes with perfluoro ketones and chloro perfluoro ketones. J Org Chem 32(2):347-352 (1967).
U.S. Appl. No. 14/369,982 Office Action dated Mar. 8, 2016.
U.S. Appl. No. 14/369,982 Office Action dated Oct. 22, 2015.
U.S. Appl. No. 14/599,105 Office Action dated Apr. 8, 2015.
U.S. Appl. No. 15/072,229 First Action Interview dated Sep. 19, 2016.
U.S. Appl. No. 15/072,229 Office Action dated Jan. 10, 2017.
U.S. Appl. No. 15/272,313 Office Action dated Apr. 10, 2017.
U.S. Appl. No. 15/272,313 Office Action dated Aug. 25, 2017.
U.S. Appl. No. 15/573,272 Office Action dated Dec. 14, 2018.
U.S. Appl. No. 15/814,322 Office Action dated Mar. 14, 2018.
U.S. Appl. No. 15/925,517 Office Action dated Jun. 20, 2019.
U.S. Appl. No. 16/349,142 Ex Parte Quayle Action dated Apr. 23, 2021.
U.S. Appl. No. 16/349,142 Office Action dated Oct. 16, 2020.
U.S. Appl. No. 16/563,733 Office Action dated Jun. 11, 2020.
U.S. Appl. No. 16/717,813 Office Action dated May 29, 2020.
Volicer et al. Effects of dronabinol on anorexia and disturbed behavior in patients with Alzheimer's disease. Int J Geriatr Psychiatry 12(9):913-919 (1997).
Wade. Deuterium isotope effects on noncovalent interactions between molecules. Chem Biol Interact 117:191-217 (1999).
Walther et al. Randomized, controlled crossover trial of dronabinol, 2.5 mg, for agitation in 2 patients with dementia. J Clin Psychopharmacol 31(2):256-258 (2011).
Ware et al. The effects of nabilone on sleep in fibromyalgia: results of a randomized controlled trial. Anesth Analg 110(2):604-610 (2010).
Whiting et al. Cannabinoids for Medical Use: A Systematic Review and Meta-analysis. JAMA 313(24):2456-2473 (2015).

(56) References Cited

OTHER PUBLICATIONS

Zajicek et al. Cannabinoids for treatment of spasticity and other symptoms related to multiple sclerosis (CAMS study): multicentre randomised placebo-controlled trial. Lancet 362(9395):1517-1526 (2003).
Zello et al. Plasma and urine enrichments following infusion of L-[1-13C]phenylalanine and L-[ring-2H5]phenylalanine in humans: evidence for an isotope effect in renal tubular reabsorption. Metabolism 43:487-491 (1994).
Co-pending U.S. Appl. No. 18/053,582, inventors CISAR; Justin S. et al., filed on Nov. 8, 2022.
PCT/IB2021/000277 International Search Report and Written Opinion dated Jul. 26, 2021.
U.S. Appl. No. 17/195,351 Office Action dated Jan. 25, 2022.

\* cited by examiner

SYNTHESIS OF A MONOACYLGLYCEROL LIPASE INHIBITOR

CROSS-REFERENCE

This application claims benefit of U.S. Provisional Application No. 63/013,454, filed on Apr. 21, 2020, which is herein incorporated by reference in its entirety.

FIELD OF THE INVENTION

The present invention relates to the manufacture of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof.

BACKGROUND OF THE INVENTION 1,1,1,3,3,3-hexafluoropropan-2-yl 4-(2-(pyrrolidin-1-yl)-4-(trifluoromethyl)benzyl)piperazine-1-carboxylate is a monoacylglycerol lipase (MAGL) inhibitor. MAGL inhibitors has been suggested for use in treating a variety of neurological and psychiatric disorders such as anxiety and pain.

WO2013/103973 discloses 1,1,1,3,3,3-hexafluoropropan-2-yl 4-(2-(pyrrolidin-1-yl)-4-(trifluoromethyl)benzyl)piperazine-1-carboxylate may be prepared starting from tert-butyl piperazine-1-carboxylate via the intermediate tert-Butyl 4-[[2-(Pyrrolidin-1-yl)-4-(trifluoromethyl)phenyl]methyl]piperazine-1-carboxylate. However, this process was not optimal with respect to parameters relevant for industrial scale applicability.

WO2018/093953 discloses the manufacture of 1,1,1,3,3,3-hexafluoropropan-2-yl 4-(2-(pyrrolidin-1-yl)-4-(trifluoromethyl)benzyl)piperazine-1-carboxylate mono-hydrochloride salt form 2. However, the process disclosed is not optimal in regard to further pharmaceutical development with respect to parameters such as processability and production on an industrial scale.

Hence, there is a need for an alternative to the current manufacturing processes of 1,1,1,3,3,3-hexafluoropropan-2-yl 4-(2-(pyrrolidin-1-yl)-4-(trifluoromethyl)benzyl)piperazine-1-carboxylate, or pharmaceutically acceptable salts thereof with respect to parameters such as applicability for industrial scale.

SUMMARY OF THE INVENTION

With this background it is an object of the present invention to provide a process that meet one or more needs described above, that is, i.a to provide a process that is suitable for further pharmaceutical development of 1,1,1,3,3,3-hexafluoropropan-2-yl 4-(2-(pyrrolidin-1-yl)-4-(trifluoromethyl)benzyl)piperazine-1-carboxylate or 1,1,1,3,3,3-hexafluoropropan-2-yl 4-(2-(pyrrolidin-1-yl)-4-(trifluoromethyl)benzyl)piperazine-1-carboxylate mono-hydrochloride salt form 2 and which is also applicable for industrial-scale production.

Accordingly, in a first aspect of the invention is provided a process for the manufacture of 1,1,1,3,3,3-hexafluoropropan-2-yl 4-(2-(pyrrolidin-1-yl)-4-(trifluoromethyl)benzyl)piperazine-1-carboxylate comprising the steps of:
a) reacting tert-butyl piperazine-1-carboxylate with hexafluoropropan-2-ol in the presence of an acyl transfer agent to form 1-(tert-butyl) 4-(1,1,1,3,3,3-hexafluoropropan-2-yl) piperazine-1,4-dicarboxylate (A2), wherein step a) is carried out in a first solvent;
b) reacting 1-(tert-butyl) 4-(1,1,1,3,3,3-hexafluoropropan-2-yl) piperazine-1,4-dicarboxylate (A2) obtained in step a) with a strong acid to form 1,1,1,3,3,3-hexafluoropropan-2-yl piperazine-1-carboxylate(A3), or a pharmaceutically acceptable salt thereof, wherein step b) is optionally carried out in a second solvent;
c) reacting 1,1,1,3,3,3-hexafluoropropan-2-yl piperazine-1-carboxylate (A3), or a pharmaceutically acceptable salt thereof obtained in step b) with 2-(pyrrolidin-1-yl)-4-(trifluoromethyl)benzaldehyde in the presence of a reducing agent and an organic base to form a reaction mixture comprising 1,1,1,3,3,3-hexafluoropropan-2-yl 4-(2-(pyrrolidin-1-yl)-4-(trifluoromethyl)benzyl)piperazine-1-carboxylate, wherein the reaction in step c) is carried out in a third solvent.

In a second aspect of the invention is provided a process for the manufacture of crystalline 1,1,1,3,3,3-hexafluoropropan-2-yl 4-(2-(pyrrolidin-1-yl)-4-(trifluoromethyl)benzyl)piperazine-1-carboxylate mono-hydrochloride salt form 2 comprising the steps of:

D1) dissolving 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof in a sixth solvent at a temperature of 38-70° C., preferably 38-42° C., optionally under stirring;

D2) converting the 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof into 1,1,1,3,3,3-hexafluoropropan-2-yl 4-(2-(pyrrolidin-1-yl)-4-(trifluoromethyl)benzyl)piperazine-1-carboxylate mono-hydrochloride salt by addition of HCl, optionally under stirring at a temperature of 70-76° C., more preferably at a temperature of 74-76° C.;

D3) optionally filtering the solution obtained in step D2)

D4) cooling the solution to 63-69° C., more preferably to temperature of 65-68° C., and adding seed crystals of 1,1,1,3,3,3-hexafluoropropan-2-yl 4-(2-(pyrrolidin-1-yl)-4-(trifluoromethyl)benzyl)piperazine-1-carboxylate mono-hydrochloride salt form 2;

D5) optionally, stirring the suspension for at least 1 hour;

D6) cooling the suspension from 63-69° C. to a temperature of 10-40° C., preferably at a temperature of 16-23° C. during a period between 12-20 hours under stirring. Other aspects, features and advantages of the methods and intermediates described herein will become apparent from the following detailed description. The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose. The invention will now be described in greater details. Each specific embodiment and variation of features applies equally to each aspect of the invention unless specifically stated otherwise.

INCORPORATION BY REFERENCE

All publications and patent applications mentioned in this specification are herein incorporated by reference to the extent applicable and relevant.

DETAILED DESCRIPTION OF THE INVENTION

The compound, 1,1,1,3,3,3-hexafluoropropan-2-yl 4-(2-(pyrrolidin-1-yl)-4-(trifluoromethyl)benzyl)piperazine-1-carboxylate, designated herein as Compound I, has the structure:

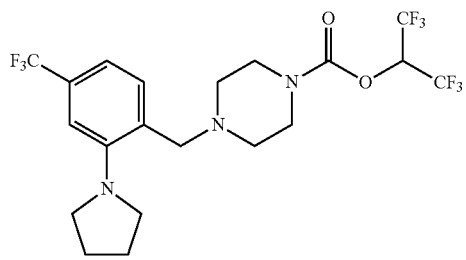 [SMILES: O=C(OC(C(F)(F)F)C(F)(F)F)N1CCN(Cc2ccc(C(F)(F)F)cc2N2CCCC2)CC1]

The compound 1,1,1,3,3,3-hexafluoropropan-2-yl 4-(2-(pyrrolidin-1-yl)-4-(trifluoromethyl)benzyl)piperazine-1-carboxylate mono-hydrochloride salt, designated herein as Compound I-HCl, has the structure:

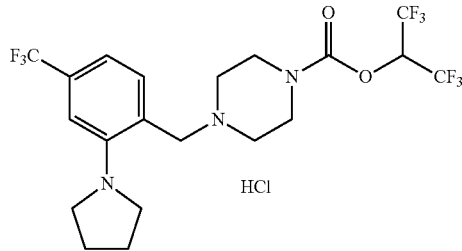 [SMILES: O=C(OC(C(F)(F)F)C(F)(F)F)N1CCN(Cc2ccc(C(F)(F)F)cc2N2CCCC2)CC1 ; Cl]

WO2018/093953 discloses crystalline 1,1,1,3,3,3-hexafluoropropan-2-yl 4-(2-(pyrrolidin-1-yl)-4-(trifluoromethyl)benzyl)piperazine-1-carboxylate mono-hydrochloride salt Form 2, designated herein as Compound I-HCl form 2.

Figure 1:
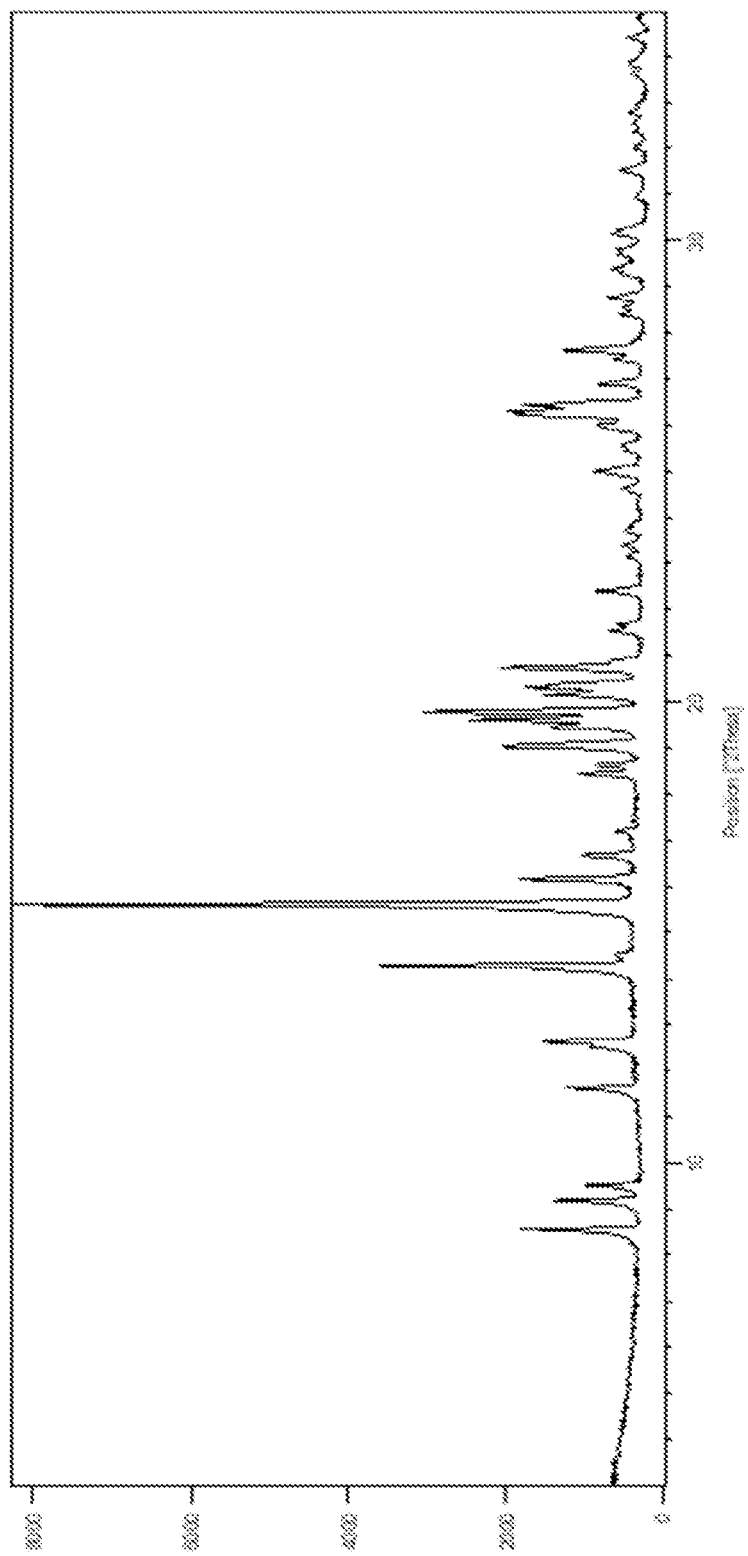
FIG. 1 Illustrates an XRPD pattern of crystalline 1,1,1,3,3,3-hexafluoropropan-2-yl 4-(2-(pyrrolidin-1-yl)-4-(trifluoromethyl)benzyl)piperazine-1-carboxylate mono-hydrochloride form 2.
Figure 2:
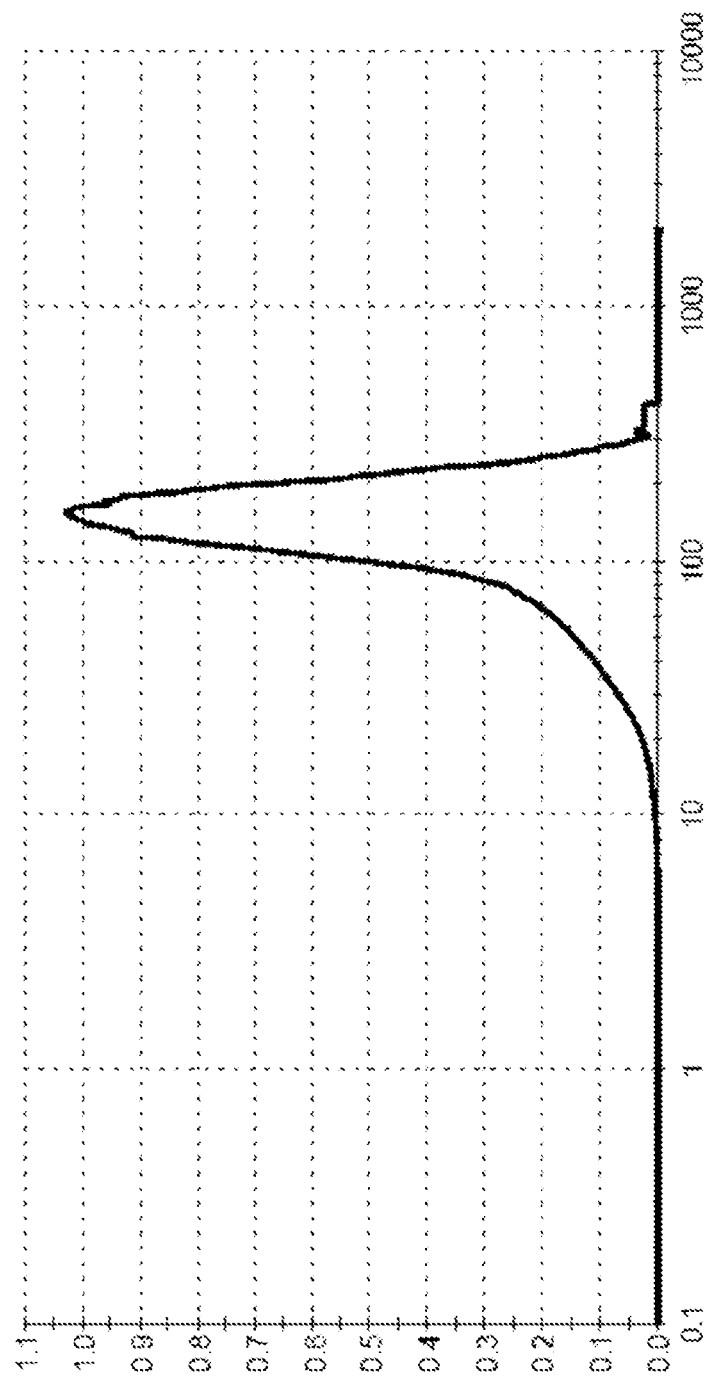
FIG. 2 Illustrates the cumulative distribution curve of a Compound I-HCl form 2 particles made by the process according to the invention, wherein the Compound I-HCl form 2 particles has been subjected to a milling step.

In an embodiment of the invention, Compound I-HCl form 2 is identifiable by an X-ray powder diffraction (XRPD) pattern with characteristic peaks at 8.6° 2-Theta, 14.3° 2-Theta, 15.6° 2-Theta, 19.0° 2-Theta, 19.8° 2-Theta, and 20.7° 2-Theta. The XRPD pattern of Compound I-HCl form 2 is shown in FIG. 1. In another embodiment of the invention, Compound I-HCl form 2 is identifiable by an X-ray powder diffraction (XRPD) pattern with characteristic peaks at 8.6° 2-Theta, 9.2° 2-Theta, 9.5° 2-Theta, 11.7° 2-Theta, 12.6° 2-Theta, 14.3° 2-Theta, 15.6° 2-Theta, 16.2° 2-Theta, 16.7° 2-Theta, 17.2° 2-Theta, 18.5° 2-Theta, 19.0° 2-Theta, 19.6° 2-Theta, 19.8° 2-Theta, 20.4° 2-Theta, 20.7° 2-Theta, 21.6° 2-Theta, 22.5° 2-Theta, 23.5° 2-Theta, and 27.7° 2-Theta.

The compound tert-butyl piperazine-1-carboxylate, designated herein as A1, has the structure:

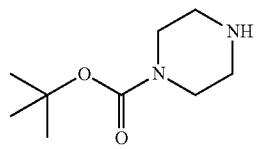

The compound 1-(tert-butyl) 4-(1,1,1,3,3,3-hexafluoropropan-2-yl) piperazine-1,4-dicarboxylate, designated herein as A2, has the structure:

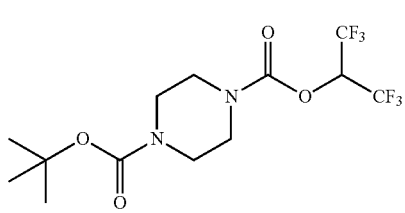

The compound 1,1,1,3,3,3-hexafluoropropan-2-yl piperazine-1-carboxylate, designated herein as A3, has the structure:

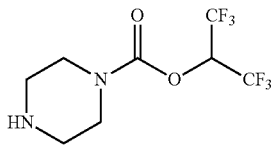

The compound 1,1,1,3,3,3-hexafluoropropan-2-yl piperazine-1-carboxylate monohydrochloride, designated herein as A3-HCl, has the structure:

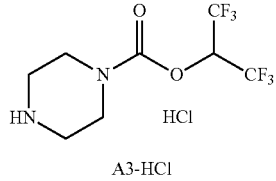 [SMILES: O=C(OC(C(F)(F)F)C(F)(F)F)N1CCNCC1 ; Cl]

The compound 1,1,1,3,3,3-hexafluoropropan-2-yl piperazine-1-carboxylate monotrifluoroacetic acid, designated herein as A3-TFA, has the structure:

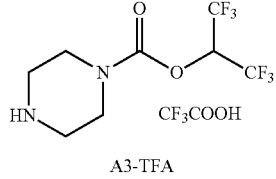

The compound 2-fluoro-4-(trifluoromethyl)benzaldehyde, designated herein as A4, has the structure:

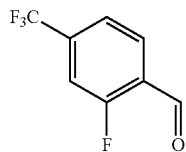

A4

The compound 2-(pyrrolidin-1-yl)-4-(trifluoromethyl)benzaldehyde, designated herein as A5, has the structure:

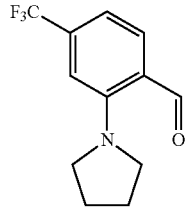

A5

The inventors have found a new synthesis for manufacturing 1,1,1,3,3,3-hexafluoropropan-2-yl 4-(2-(pyrrolidin-1-yl)-4-(trifluoromethyl)benzyl)piperazine-1-carboxylate by coupling A3 and A5 via a reductive amination.

The invention provides a scalable synthesis of Compound I with high yield and use of less toxic solvents. The overall process is illustrated in brief below. Compound I may in a further embodiment be crystallized to Compound I-HCl form 2.

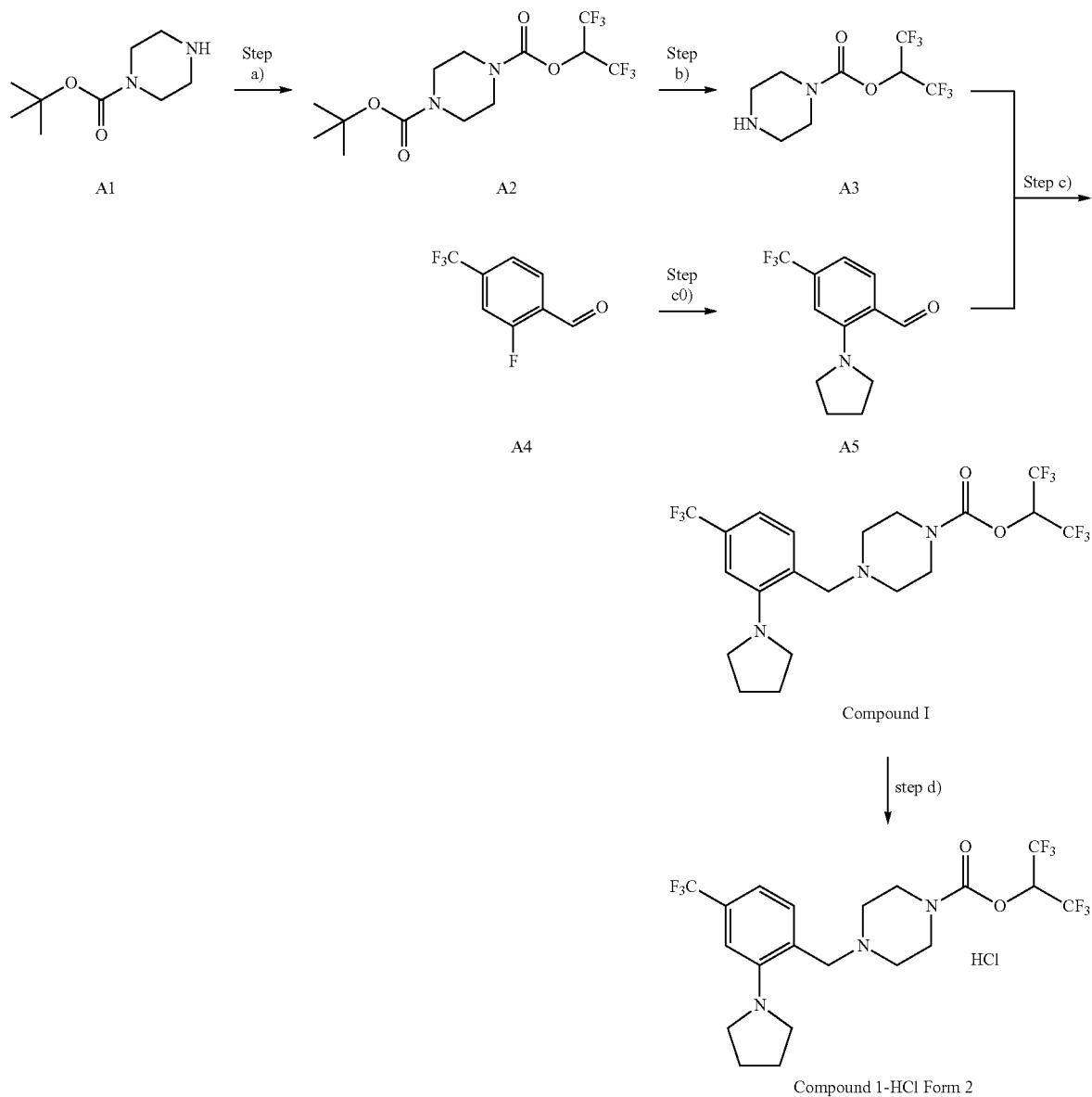

Step a) is a carbamate formation by reacting A1 with hexafluoropropan-2-ol in the presence of an acyl transfer agent such as 1,1'-carbonyldiimidazole (CDI) to form A2. The formation of A2 has previously been disclosed in WO2013/103973. However, the inventors have surprisingly found that the formation of A2 can advantageously be carried out under increased pressure in a solvent allowing the use of less HFIP and avoiding oiling during precipitation. Furthermore, the yield of A2 can be obtained in high yield by adding the reactants in the order of acyl transfer agent, solvent and A1, respectively to limit formation of side products.

Step b) is a deprotection step, wherein the piperazine moiety of A2 is liberated by a reaction between A2 and a strong acid. The formation of A3 have previously been disclosed in WO2013/103973, wherein TFA is added to A2 to provide A3-TFA. The inventors found that in order to control the flammable isobutene evolution, the TFA was charged first followed by slow addition of A2. Surprisingly, the inventors found that heating the solution to about 35-50° C. during the crystallization step with water as antisolvent allowed for a more controlled crystallization and thereby leading to a product that could be easily isolated.

Alternatively, the inventors found that TFA could be substituted with HCl to directly precipitate A3 as A3-HCl that was advantageously non-hygroscopic and an easy to filter solid, which provided a high yield and lower manufacturing costs. Furthermore, HCl is preferred to use in an industrial scale due to its ease to use in manufacture in industrial scale and low cost. In an embodiment of the invention, gaseous HCl was used facilitating a one pot process for the manufacture of A3-HCl.

Step c0) is a nucleophilic aromatic substitution by reacting A4 with pyrrolidine to afford A5. The formation of A5 have previously been disclosed in J. Med. Chem. 2018, 61, 9062-9084, wherein A5 was charged in a flask with pyrrolidine, potassium carbonate and DMSO with a yield of 63% after extraction with DCM and purification over silica gel. To make the process more scalable both in regards to cost and safety, the inventors found that step c0) could advantageously be carried out in ethyl acetate as solvent.

Step c) is a reductive amination step to provide Compound I. In a method disclosed in J. Med. Chem. 2018, 61, 9062-9084, Compound I was provided by reacting A3 and tert-butyl piperazine-1-carboxylate to afford tert-butyl 4-(2-(pyrrolidin-1-yl)-4-(trifluoromethyl)benzyl)piperazine-1-carboxylate, followed by deprotection with TFA and a reaction with hexafluoropropan-2-ol to afford compound I with a yield of 77%. The process disclosed in J. Med. Chem. 2018, 61, 9062-9084 is not suitable for industrial scale-up as the process utilize toxic solvents such as DCM, and product isolation from silica gel chromatography, which is a costly process and not easily applicable on large scale. In the present invention, Compound I is provided by a reductive amination between A3 and A5 in the presence of reduction agent without the use of DCM, and surprisingly the final product can be isolated with a yield up to 92%. The inventors found that by using the same solvent in step c0) and step c) there was no need for an additional solvent swap between step c0) and step c) making the process more environmentally friendly. Advantageously the use of ethyl acetate as solvent in step c0) and c), led to a more cost-effective manufacture of Compound I in high yields. Preferably, when ethyl acetate is used in step c), an isolation step comprising an aqueous work-up may be used to afford Compound I in a high yield.

Step d) is the salt formation of Compound I-HCl form 2 by reacting Compound I with a HCl solution in a solvent such as isopropanol. The formation of Compound I-HCl form 2 is disclosed in WO2018/093953 wherein Compound I-HCl form 2 is provided by reacting Compound I with HCl in solvents such as ethanol or acetone. The process of WO2018/093953 led to preparation of Compound I-HCl form 2 particles having a particle size distribution (PSD) that was not reproduceble between batches and not suitable for manufacturing of finished dosage form such as a tablet comprising Compound I-HCl form 2.

From a pharmaceutical manufacturing point of view and especially manufacturing of tablets a reproducible and controlled PSD are highly desirable. In a preferred embodiment, Compound I-HCl form 2 particles is characterized by having a d10 particle size between 10-30 µm, a d50 particle size between 60-80 µm and a d90 particle size below 200 µm.

In comparison, the process for manufacturing Compound I-HCl form 2 described in the prior art provided a d10 particle size down to 5 am and a particle size d90 up to 300 µm giving a wide distribution curve, which is not desirable when manufacturing a solid dosage form such as a tablet comprising Compound I-HCl form 2. One known solution to obtain particles with an appropriate PSD is to subject a particles to multiple sieve steps in order to end of with an acceptable PSD. However, such solution has the drawback of wasting high amounts of product which is both expensive and also not environmentally friendly.

In a preferred embodiment, the inventors surprisingly found that Compound I-HCl form 2 may be crystallized from Compound I by a controlled crystallization process comprising very specific reaction and cooling temperatures to provide Compound I-HCl form 2 particles suitable for large scale production and providing particles suitable for further processing.

Definitions

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

The term "acceptable" or "pharmaceutically acceptable", with respect to an ingredient, as used herein, means having no persistent detrimental effect on the general health of the subject being treated or does not abrogate the biological activity or properties of the compound, and is relatively nontoxic.

The term "$C_1$-$C_4$ alcohol", as used herein, refers to a straight or branched, saturated hydrocarbon chain containing from 1 to 4 carbon atoms, wherein in at least one —OH group is appended to the hydrocarbon chain. $C_1$-$C_4$ alcohol include, but are not limited to methanol, ethanol, isopropanol (2-propanol), propanol, butanol, and 2-methylpropan-1-ol.

The terms "inhibits", "inhibiting", or "inhibitor" of an enzyme as used herein, refer to inhibition of enzymatic activity.

The term "isolation step", as used herein, refers to separating and removing a component of interest from components not of interest. Isolation strategies are known in the art and may include concentrating the desired component by heat, solid isolation by filtering, and centrifugation or a combination thereof, which may be followed by a suitable drying step.

The term "washing step", as used herein, refers to a step of adding one or more solvents for removing impurities from a desired product/intermediate or mixture comprising the desired product/intermediate.

The term "isolated compound", as used herein, refers to compound that has been subjected to an isolation step removing the compound of interest from components not of interest. Isolated compounds can be in either a dry or semi-dry state. An isolated compound will generally have a purity between 96-99%. In an embodiment of the invention the purity of an isolated compound is above 98%.

The term "drying step", as used herein, refers to a step of vaporization and removal of water or other liquids from a solution, wet cake, suspension, or other solid-liquid mixture to form a dry solid. drying strategies as such is known in the art and can be done providing heat to solution causing the impurities to evaporate, preferably the drying is done under vacuum.

The term "crystallisation" or "crystallisation step", as used herein, refers to the use of a crystallisation technology to solidify the component of interest in a mixture. The mixtures are typically in the form of a solution, suspension or colloids. Crystallization technologies include but are not limited to cooling, evaporation, antisolvent. Optionally, the crystallisation step may be carried out in the presence of a seed crystal.

The term "solvent", as used herein, refers to a suitable solvent, or mixture of solvents, inert to the ongoing reaction that sufficiently solubilizes the reactants to afford a medium within which to affect the desired reaction.

The term "aprotic solvent", as used herein, refers to a solvent that is relatively inert to proton activity, i.e. not acting as a proton donor. Examples include but are not limited to hydrocarbons such as toluene and, heterocyclic compound such as tetrahydrofuran, haloalkanes such as dichloromethane, ethers such as methyl tert-butyl ether.

The term "strong acid", as used herein, refers to an acidic compound having a pKa in water at a temperature of 25° C. of at most 1.

The term "acyl transfer agent", as used herein, refers to an additive useful in the transfer of an acyl group in the preparation of a carbamate group starting from an amine such as piperazine. Acyl transfer agents include but are not limited to phosgene, diphosgene, triphosgene, 1,1'-carbonyldiimidazole, N,N'-dicyclohexylcarbodiimide, and 1-ethyl-3-(3-dimethylaminopropyl)carbodiimide.

The term "organic base", as used herein, refers to term organic compound containing one or more nitrogen atoms, and which acts as a base. Examples of organic bases are, but not limited to, triethylamine, 4-methylmorpholine, pyridine, lutidine, 1,4-Diazabicyclo[2.2.2]octane (DABCO), 1,8-Diazabicyclo [5.4.0] undec-7-ene (DBU), 1,2,2,6,6-pentamethylpiperidine, 1,1,3,3-tetramethylguanidine and N-ethyldiisopropylamine (DIPEA).

The term "particle size distribution" (PSD) as used herein refers to the mean particle size from a statistical distribution of a range of particle sizes. The Compound I-HCl form 2 particle size distribution, in particular d90, d50, d10 values, may be determined by well-known methods of the prior art such as sieve analysis, laser diffraction methods, image analysis or optical counting methods.

As illustrated in the Example 15, the particle size distribution can be measured by image analysis.

As used herein, by "d90 particle size" refers to the particle diameter wherein 90 percent of the particle population has a diameter below such value.

As used herein, by "d50 particle size" refers to the median particle diameter, wherein half of the particle population has a diameter below such value.

As used herein, by "d10 particle size" refers to the particle diameter wherein 10 percent of the particle population has a diameter below such value.

The term "stirring", as used herein, refers to the process of mixing a solution, suspension or another liquid-liquid system or liquid-solid system. The mixing is preferably done by a stirrer or an impeller in a large-scale production.

The term "stirring rate", as used herein, refers to revolutions per minute of an impeller or stirrer. It is within the knowledge of the skilled person to determine the rate of stirring depending on the equipment available (size of vessel and size of impeller) and task to be accomplished.

The term "reducing agent", as used herein, refers to any compound or complex that is known in the field for its effects in converting a functional group in a molecule from one oxidation state to a lower oxidation state. Examples of a reducing agent may be but not limited to sodium triacetoxyborohydride, sodium borohydride, lithium aluminium hydride, hydrogen ($H_2$) in presence of Pd/C, $H_2$ in presence of Rh/C in, and sodium cyanoborohydride.

Embodiments of the Invention

In the following, embodiments of the invention are disclosed. The first embodiment is denoted E1, the second embodiment is denoted E2 and so forth.

E1. A process for the manufacture of 1,1,1,3,3,3-hexafluoropropan-2-yl 4-(2-(pyrrolidin-1-yl)-4-(trifluoromethyl)benzyl)piperazine-1-carboxylate comprising the steps of:
a) reacting tert-butyl piperazine-1-carboxylate (A1) with hexafluoropropan-2-ol in the presence of an acyl transfer agent to form 1-(tert-butyl) 4-(1,1,1,3,3,3-hexafluoropropan-2-yl) piperazine-1,4-dicarboxylate (A2), wherein step a) is carried out in a first solvent;
b) reacting 1-(tert-butyl) 4-(1,1,1,3,3,3-hexafluoropropan-2-yl) piperazine-1,4-dicarboxylate (A2) obtained in step a) with a strong acid to form 1,1,1,3,3,3-hexafluoropropan-2-yl piperazine-1-carboxylate (A3), or a pharmaceutically acceptable salt thereof, wherein step b) is optionally carried out in a second solvent;
c) reacting 1,1,1,3,3,3-hexafluoropropan-2-yl piperazine-1-carboxylate (A3), or a pharmaceutically acceptable salt thereof obtained in step b) with 2-(pyrrolidin-1-yl)-4-(trifluoromethyl)benzaldehyde in the presence of a reducing agent and an organic base to form a reaction mixture comprising 1,1,1,3,3,3-hexafluoropropan-2-yl 4-(2-(pyrrolidin-1-yl)-4-(trifluoromethyl)benzyl)piperazine-1-carboxylate, wherein the reaction in step c) is carried out in a third solvent;

E2. The process according to embodiment E1, wherein step a) is carried out at around a pressure of 2 bar to 6 bar, preferably 4 bar.

Surprisingly, the formation of A2 can advantageously be carried out under increased pressure in a first solvent allowing the use of less HFIP and avoiding oiling during precipitation E3. The process according to any one of embodiments E1-E2, wherein the acyl transfer agent in step a) is selected from the group consisting of phosgene, diphosgene, triphosgene, 1,1'-carbonyldiimidazole, N,N'-dicyclohexylcarbodiimide, and 1-ethyl-3-(3-dimethylaminopropyl)carbodiimide.

E4. The process according to any one of embodiments E1-E3, wherein the acyl transfer agent in step a) is 1,1'-carbonyldiimidazole.

E5. The process according to any one of embodiments E1-E4, wherein the first solvent in step a) is an aprotic solvent.

E6. The process according to any one of embodiments E1-E5, wherein the ingredients in step a) are added in the consecutive order of the acyl transfer agent, the first solvent, tert-butyl piperazine-1-carboxylate (A1), and hexafluoropropan-2-ol.

Surprisingly, A2 can be obtained in high yield by adding the reactants in the order of acyl transfer agent, solvent and A1, respectively to limit formation of side products.

E7. The process according to any one of embodiments E1-E6, wherein the first solvent in step a) is selected from the group consisting of acetonitrile, dichloromethane, methyl tert-butyl ether, tetrahydrofuran and toluene.

E8. The process according to any one of embodiments E1-E7, wherein the first solvent in step a) is acetonitrile.

E9. The process according to any one of embodiments E1-E8, wherein the strong acid in step b) is selected from trifluoroacetic acid or HCl.

E10. The process according to any one of embodiments E1-E9, wherein the strong acid in step b) is trifluoroacetic acid, and the ingredients in step b) are added in the consecutive order of trifluoroacetic acid followed by 1-(tert-butyl) 4-(1,1,1,3,3,3-hexafluoropropan-2-yl) piperazine-1,4-dicarboxylate (A2) to form a mixture comprising 1,1,1,3,3,3-hexafluoropropan-2-yl piperazine-1-carboxylate (A3), or a pharmaceutically acceptable salt thereof and trifluoroacetic acid.

E11. The process according to any one of embodiments E1-E10, wherein 1-(tert-butyl) 4-(1,1,1,3,3,3-hexafluoropropan-2-yl) piperazine-1,4-dicarboxylate (A2) in step b) is added to trifluoroacetic acid at around 10-30° C. to form the mixture comprising 1,1,1,3,3,3-hexafluoropropan-2-yl piperazine-1-carboxylate (A3), or a pharmaceutically acceptable salt thereof and trifluoroacetic acid.

E12. The process according to embodiment E11, wherein 1-(tert-butyl) 4-(1,1,1,3,3,3-hexafluoropropan-2-yl) piperazine-1,4-dicarboxylate (A2) is added to trifluoroacetic acid over at least 3 hours.

E13. The process according to any one of embodiments E11-E12, wherein step b) is carried out in a closed system equipped with a hopper.

E14. The process according to any one of embodiments E1-E13, wherein step b) comprise the step comprising adding water to the mixture comprising 1,1,1,3,3,3-hexafluoropropan-2-yl piperazine-1-carboxylate (A3), or a pharmaceutically acceptable salt thereof and trifluoroacetic acid to form a suspension.

E15. The process according to embodiment E14, wherein the water in step b) is added at 35-50° C.

E16. The process according to any one of embodiments E1-E9, wherein the strong acid in step b) is HCl; and wherein step b) is carried out in a second solvent.

E17. The process according to embodiment E16, wherein the second solvent in step b) is selected from the group consisting of toluene, isopropyl acetate, dichloromethane, acetonitrile, ethers and esters.

E18. The process according to any one of embodiments E16-E17, wherein the second solvent in step b) is isopropyl acetate.

E19. The process according to any one of embodiments E1-E18, wherein step b) further comprise a step of isolating 1-(tert-butyl) 4-(1,1,1,3,3,3-hexafluoropropan-2-yl) piperazine-1,4-dicarboxylate (A2), or a pharmaceutically acceptable salt thereof.

E20. The process according to any one of embodiments E1-E19, wherein the compound 1,1,1,3,3,3-hexafluoropropan-2-yl piperazine-1-carboxylate (A3), or a pharmaceutically acceptable salt thereof in step b) is obtained as 1,1,1,3,3,3-hexafluoropropan-2-yl piperazine-1-carboxylate monotrifluoroacetic acid salt.

E21. The process according to any one of embodiments E1-E20, wherein the compound 1,1,1,3,3,3-hexafluoropropan-2-yl piperazine-1-carboxylate (A3), or a pharmaceutically acceptable salt thereof in step b) is obtained as 1,1,1,3,3,3-hexafluoropropan-2-yl piperazine-1-carboxylate mono-hydrochloride salt.

E22. The process according to any one of embodiments E1-E21, wherein the third solvent in step c) is selected from the group consisting of dichloromethane, acetonitrile, tetrahydrofuran, dimethylformamide and ethyl acetate.

E23. The process according to any one of embodiments E1-E22, wherein the third solvent in step c) is ethyl acetate.

E24. The process according to any one of embodiments E1-E23, wherein the reducing agent in step c) is selected from the group consisting of sodium triacetoxyborohydride, $H_2$ in the presence of a catalyst such as Pd/C, Pt/C, Rh/C, sodium borohydride and sodium cyanoborohydride E25. The process according to any one of embodiments E1-E24, wherein the reducing agent in step c) is sodium triacetoxyborohydride.

E26. The process according to any one of embodiments E1-E25, wherein the organic base in step c) is selected from the group consisting of triethylamine, N,N-diisopropylethylamine, pyridine, and 2,6-lutidine.

E27. The process according to any one of embodiments E1-E26, wherein the organic base in step c) is triethylamine.

E28. The process according to any one of embodiments E1-E27, wherein step c) comprises the steps of:

i) providing a mixture comprising 1,1,1,3,3,3-hexafluoropropan-2-yl piperazine-1-carboxylate (A3), or a pharmaceutically acceptable salt thereof obtained in step b), 2-(pyrrolidin-1-yl)-4-(trifluoromethyl)benzaldehyde, the organic base, and the third solvent;

ii) adding the reducing agent to the mixture obtained from step i) to provide a reaction mixture comprising 1,1,1,3,3,3-hexafluoropropan-2-yl 4-(2-(pyrrolidin-1-yl)-4-(trifluoromethyl)benzyl)piperazine-1-carboxylate.

E29. The process according to any one of embodiments E1-E28, wherein step c) further comprises step of:

iia) isolating 1,1,1,3,3,3-hexafluoropropan-2-yl 4-(2-(pyrrolidin-1-yl)-4-(trifluoromethyl)benzyl)piperazine-1-carboxylate from the reaction mixture in step c).

E30. The process according to any one of embodiments E1-E29, wherein step c) further comprises the step of:

iii) adding water to the reaction mixture comprising 1,1,1,3,3,3-hexafluoropropan-2-yl 4-(2-(pyrrolidin-1-yl)-4-(trifluoromethyl)benzyl)piperazine-1-carboxylate to form a phase separation having an organic phase comprising 1,1,1,3,3,3-hexafluoropropan-2-yl 4-(2-(pyrrolidin-1-yl)-4-(trifluoromethyl)benzyl)piperazine-1-carboxylate, followed by diluting the organic phase with the third solvent.

E31. The process according to embodiment E30, wherein step c) further comprises the steps of:
iv) adding an $C_1$-$C_4$ alcohol to the organic phase comprising 1,1,1,3,3,3-hexafluoropropan-2-yl 4-(2-(pyrrolidin-1-yl)-4-(trifluoromethyl)benzyl)piperazine-1-carboxylate to provide a solution comprising 1,1,1,3,3,3-hexafluoropropan-2-yl 4-(2-(pyrrolidin-1-yl)-4-(trifluoromethyl)benzyl)piperazine-1-carboxylate, optionally concentrating the solution.
v) adding water to the solution comprising 1,1,1,3,3,3-hexafluoropropan-2-yl 4-(2-(pyrrolidin-1-yl)-4-(trifluoromethyl)benzyl)piperazine-1-carboxylate to form a suspension comprising 1,1,1,3,3,3-hexafluoropropan-2-yl 4-(2-(pyrrolidin-1-yl)-4-(trifluoromethyl)benzyl)piperazine-1-carboxylate.

E32. The process according to embodiment E31, wherein the $C_1$-$C_4$ alcohol is isopropanol or methanol.

E33. The process according to embodiments E31-E32, wherein the $C_1$-$C_4$ alcohol is methanol.

E34. The process according to embodiment E33, wherein the $C_1$-$C_4$ alcohol is isopropanol.

E35. The process according to any one of embodiments E31-E34, wherein step c) further comprises the step of:
vi) isolating 1,1,1,3,3,3-hexafluoropropan-2-yl 4-(2-(pyrrolidin-1-yl)-4-(trifluoromethyl)benzyl)piperazine-1-carboxylate from the suspension comprising 1,1,1,3,3,3-hexafluoropropan-2-yl 4-(2-(pyrrolidin-1-yl)-4-(trifluoromethyl)benzyl)piperazine-1-carboxylate obtained in step v).

E36. The process according to any one of embodiments E1-E35, wherein 2-(pyrrolidin-1-yl)-4-(trifluoromethyl)benzaldehyde is provided to step c) as a solution comprising 2-(pyrrolidin-1-yl)-4-(trifluoromethyl)benzaldehyde and a fourth solvent.

E37. The process according to any one of embodiments E1-E36, wherein 2-(pyrrolidin-1-yl)-4-(trifluoromethyl)benzaldehyde is obtained in step c0) prior to step c), wherein step c0) comprises the step of: reacting 2-fluoro-4-(trifluoromethyl)benzaldehyde with pyrrolidine in the presence of an inorganic base to form 2-(pyrrolidine-1-yl)-4-(trifluoromethyl)benzaldehyde, wherein the reaction in step c0) is carried out in the fourth solvent.

E38. The process according to embodiment E37, wherein the inorganic base in step c0) is an alkali metal carbonate or an alkali metal bicarbonate.

E39. The process according to any one of embodiments E37-E38, wherein the inorganic base in step c0) is $Na_2CO_3$.

E40. The process according to any one of embodiments E37-E39, wherein the fourth solvent in step c0) is selected from the group consisting of ethyl acetate, acetonitrile, dichloromethane, dimethylformamide and tetrahydrofuran.

E41. The process according to any one of embodiments E37-E40, wherein the fourth solvent is ethyl acetate.

E42. The process according to any one of embodiments E1-E41, wherein the third and the fourth solvent is ethyl acetate.

Advantageously the use of ethyl acetate as solvent in step c0) and c), led to a more cost-effective manufacture of Compound I in high yields.

E43. The process according to any one of embodiments E37-42, wherein the inorganic base and the fourth solvent in step c0) are $Na_2CO_3$ and ethyl acetate.

E44. The process according to any one of embodiments E37-E43, wherein step c0) further comprises adding around 1-2% w/w of water to the mixture obtained step c0) comprising ethyl acetate and 2-(pyrrolidine-1-yl)-4-(trifluoromethyl)benzaldehyde.

Surprisingly, the addition of a small amount of water increases the reaction rate and conversion of step c).

E45. The process according to any one of embodiments E37-E44, wherein 2-(pyrrolidine-1-yl)-4-(trifluoromethyl) benzaldehyde in step c0) is obtained in a solution comprising 2-(pyrrolidin-1-yl)-4-(trifluoromethyl)benzaldehyde and the fourth solvent.

E46. A process for the manufacture of 1,1,1,3,3,3-hexafluoropropan-2-yl 4-(2-(pyrrolidin-1-yl)-4-(trifluoromethyl)benzyl)piperazine-1-carboxylate comprising the steps of:
a) reacting tert-butyl piperazine-1-carboxylate (A1) with hexafluoropropan-2-ol in the presence of an acyl transfer agent to form 1-(tert-butyl) 4-(1,1,1,3,3,3-hexafluoropropan-2-yl) piperazine-1,4-dicarboxylate (A2), wherein step a) is carried out in a first solvent;
b) reacting 1-(tert-butyl) 4-(1,1,1,3,3,3-hexafluoropropan-2-yl) piperazine-1,4-dicarboxylate (A2) obtained in step a) with HCl to form a 1,1,1,3,3,3-hexafluoropropan-2-yl piperazine-1-carboxylate, or a pharmaceutically acceptable salt thereof; wherein step b) is carried out in isopropyl acetate;
c) reacting 1,1,1,3,3,3-hexafluoropropan-2-yl piperazine-1-carboxylate (A3), or a pharmaceutically acceptable salt thereof obtained in step b) with 2-(pyrrolidin-1-yl)-4-(trifluoromethyl)benzaldehyde in the presence of a reducing agent and an organic base to form a reaction mixture comprising 1,1,1,3,3,3-hexafluoropropan-2-yl 4-(2-(pyrrolidin-1-yl)-4-(trifluoromethyl)benzyl)piperazine-1-carboxylate, wherein the reaction in step c) is carried out in ethyl acetate;

E47. The process according to embodiment E46, wherein step a) is carried out at a pressure of around 4 bar.

E48. The process according to any one of embodiments E46-E47, wherein the acyl transfer agent in step a) is 1,1'-carbonyldiimidazole.

E49. The process according to any one of embodiments E46-E48, wherein the first solvent in step a) is acetonitrile.

E50. The process according to any one of embodiments E46-E49, wherein the reducing agent in step c) is sodium triacetoxyborohydride.

E51. The process according to any one of embodiments E46-E50, wherein the organic base is triethylamine.

E52. The process according to any one of embodiments E46-E51, wherein step b) is performed in a one-pot process and wherein HCl is in the form of gaseous HCl.

E53. The process according to any one of embodiments E46-E52, wherein the step c) comprises the steps of
i) providing a mixture comprising 1,1,1,3,3,3-hexafluoropropan-2-yl piperazine-1-carboxylate (A3), or a pharmaceutically acceptable salt thereof obtained in step b), 2-(pyrrolidin-1-yl)-4-(trifluoromethyl)benzaldehyde, the organic base, and ethyl acetate;
ii) adding the reducing agent to the mixture obtained from step i) to provide the reaction mixture comprising 1,1,1,3,3,3-hexafluoropropan-2-yl 4-(2-(pyrrolidin-1-yl)-4-(trifluoromethyl)benzyl)piperazine-1-carboxylate.

E54. The process according to any one of embodiments E46-E53, wherein step c) further comprise the step of:

iia) isolating 1,1,1,3,3,3-hexafluoropropan-2-yl 4-(2-(pyrrolidin-1-yl)-4-(trifluoromethyl)benzyl)piperazine-1-carboxylate from the reaction mixture in step c).

E55. The process according to any one of embodiments E46-E54, wherein step c) further comprises the step of:

iii) adding water to the reaction mixture comprising 1,1,1,3,3,3-hexafluoropropan-2-yl 4-(2-(pyrrolidin-1-yl)-4-(trifluoromethyl)benzyl)piperazine-1-carboxylate to form a phase separation having an organic phase comprising 1,1,1,3,3,3-hexafluoropropan-2-yl 4-(2-(pyrrolidin-1-yl)-4-(trifluoromethyl)benzyl)piperazine-1-carboxylate, followed by diluting the organic phase with ethyl acetate.

E56. The process according to any one of embodiments E46-E55, wherein the isolation step in step c) further comprises the steps of:

iv) adding an $C_1$-$C_4$ alcohol to the organic phase comprising 1,1,1,3,3,3-hexafluoropropan-2-yl 4-(2-(pyrrolidin-1-yl)-4-(trifluoromethyl)benzyl)piperazine-1-carboxylate to provide a solution comprising 1,1,1,3,3,3-hexafluoropropan-2-yl 4-(2-(pyrrolidin-1-yl)-4-(trifluoromethyl)benzyl) piperazine-1-carboxylate, optionally concentrating the solution.

v) adding water to the solution comprising 1,1,1,3,3,3-hexafluoropropan-2-yl 4-(2-(pyrrolidin-1-yl)-4-(trifluoromethyl)benzyl)piperazine-1-carboxylate to form a suspension comprising 1,1,1,3,3,3-hexafluoropropan-2-yl 4-(2-(pyrrolidin-1-yl)-4-(trifluoromethyl)benzyl)piperazine-1-carboxylate.

Advantageously an aqueous work-up can be added to step c allowing the removal of triethylamine, HCl salts and side products. The aqueous work-up combined with the use of ethyl acetate (water immiscible) allows for a more controlled crystallisation of Compound I giving a surprisingly high yield, high purity without the need of toxic solvents such as DCM, and product isolation from silica gel chromatography.

E57. The process according to embodiment E56, wherein the $C_1$-$C_4$ alcohol is isopropanol or methanol.

E58. The process according to embodiment E57, wherein the $C_1$-$C_4$ alcohol is methanol.

E59. The process according to embodiment E57, wherein the $C_1$-$C_4$ alcohol is isopropanol.

Isopropanol surprisingly showed to solubilize the impurities of the present reaction better than methanol allowing for the isolation of Compound I in higher purity compared to methanol.

E60. The process according to any one of embodiments E46-E59, wherein step c) further comprises the step of:

vi) isolating 1,1,1,3,3,3-hexafluoropropan-2-yl 4-(2-(pyrrolidin-1-yl)-4-(trifluoromethyl)benzyl)piperazine-1-carboxylate from the suspension comprising 1,1,1,3,3,3-hexafluoropropan-2-yl 4-(2-(pyrrolidin-1-yl)-4-(trifluoromethyl)benzyl)piperazine-1-carboxylate obtained in embodiment E55.

E61. The process according to any one of embodiments E46-E60, wherein 2-(pyrrolidin-1-yl)-4-(trifluoromethyl) benzaldehyde is obtained in step c0) prior to step c), wherein step c0) comprises the step of reacting 2-fluoro-4-(trifluoromethyl)benzaldehyde with pyrrolidine in the presence of an inorganic base to form 2-(pyrrolidine-1-yl)-4-(trifluoromethyl)benzaldehyde, wherein the reaction in step c0) is carried out in ethyl acetate.

E62. The process according to any one of embodiments E46-E61, wherein the inorganic base is $Na_2CO_3$.

E63. Process for the manufacture of 1,1,1,3,3,3-hexafluoropropan-2-yl 4-(2-(pyrrolidin-1-yl)-4-(trifluoromethyl) benzyl)piperazine-1-carboxylate comprising the steps of:

a) reacting tert-butyl piperazine-1-carboxylate (A1) with hexafluoropropan-2-ol in the presence of an acyl transfer agent to form 1-(tert-butyl) 4-(1,1,1,3,3,3-hexafluoropropan-2-yl) piperazine-1,4-dicarboxylate (A2), wherein step a) is carried out in a first solvent;

b) reacting 1-(tert-butyl) 4-(1,1,1,3,3,3-hexafluoropropan-2-yl) piperazine-1,4-dicarboxylate (A2) obtained in step a) with trifluoroacetic acid to form a 1,1,1,3,3,3-hexafluoropropan-2-yl piperazine-1-carboxylate (A3), or a pharmaceutically acceptable salt thereof;

c) reacting 1,1,1,3,3,3-hexafluoropropan-2-yl piperazine-1-carboxylate (A3), or a pharmaceutically acceptable salt thereof obtained in step b) with 2-(pyrrolidin-1-yl)-4-(trifluoromethyl)benzaldehyde in the presence of a reducing agent and an organic base to form 1,1,1,3,3,3-hexafluoropropan-2-yl 4-(2-(pyrrolidin-1-yl)-4-(trifluoromethyl)benzyl)piperazine-1-carboxylate, wherein the reaction in step c) is carried out in ethyl acetate.

E64. The process according to embodiment E63, wherein the ingredients in step a) are added in the consecutive order of the acyl transfer agent, the first solvent, tert-butyl piperazine-1-carboxylate (A1), and hexafluoropropan-2-ol as the last ingredient.

E65. The process according to any one of embodiments E63-E64, wherein the ingredients in step b) are added in the consecutive order of trifluoroacetic acid followed by 1-(tert-butyl) 4-(1,1,1,3,3,3-hexafluoropropan-2-yl) piperazine-1,4-dicarboxylate (A2).

E66. The process according to any one of embodiments E63-E65 wherein 1-(tert-butyl) 4-(1,1,1,3,3,3-hexafluoropropan-2-yl) piperazine-1,4-dicarboxylate (A2) in step b) is added to trifluoroacetic acid at around 10-30° C. to provide a mixture comprising 1,1,3,3,3-hexafluoropropan-2-yl piperazine-1-carboxylate, or a pharmaceutically acceptable salt thereof and trifluoroacetic acid.

E67. The process according to embodiment E66, wherein 1-(tert-butyl) 4-(1,1,1,3,3,3-hexafluoropropan-2-yl) piperazine-1,4-dicarboxylate (A2) is added to trifluoroacetic acid over at least 3 hours.

E68. The process according to any of embodiments E66-E67, wherein step b) is carried out in a closed system equipped with a hopper.

E69. The process according to any one of embodiments E66-E68, wherein step b) comprise a crystallization step comprising adding water to a mixture comprising 1,1,1,3,3,3-hexafluoropropan-2-yl piperazine-1-carboxylate (A3), or a pharmaceutically acceptable salt thereof and trifluoroacetic acid to form a suspension.

E70. The process according to embodiment E69, wherein the water is added at 35-50° C.

E71. The process according to any one of embodiments E63-E70, wherein step c) comprises the steps of:

i) providing a mixture comprising 1,1,1,3,3,3-hexafluoropropan-2-yl piperazine-1-carboxylate (A3), or a pharmaceutically acceptable salt thereof obtained in step b), 2-(pyrrolidin-1-yl)-4-(trifluoromethyl)benzaldehyde, the organic base, and ethyl acetate;

ii) adding the reducing agent to the mixture obtained from step i) to provide the reaction mixture comprising 1,1,1,3,3,3-hexafluoropropan-2-yl 4-(2-(pyrrolidin-1-yl)-4-(trifluoromethyl)benzyl)piperazine-1-carboxylate.

E72. The process according to any one of embodiments E63-E71, wherein step c) further comprises step of:

iia) isolating 1,1,1,3,3,3-hexafluoropropan-2-yl 4-(2-(pyrrolidin-1-yl)-4-(trifluoromethyl)benzyl)piperazine-1-carboxylate from the reaction mixture in step c).

E73. The process according to any one of embodiments E63-E72, wherein step c) further comprises the step of:
  iii) adding water to the reaction mixture comprising 1,1,1,3,3,3-hexafluoropropan-2-yl 4-(2-(pyrrolidin-1-yl)-4-(trifluoromethyl)benzyl)piperazine-1-carboxylate to form a phase separation having an organic phase comprising 1,1,1,3,3,3-hexafluoropropan-2-yl 4-(2-(pyrrolidin-1-yl)-4-(trifluoromethyl)benzyl)piperazine-1-carboxylate, followed by diluting the organic phase with the third solvent.

E74. The process according to embodiment E73, wherein step c) further comprises the steps of:
  iv) adding an $C_1$-$C_4$ alcohol to the organic phase comprising 1,1,1,3,3,3-hexafluoropropan-2-yl 4-(2-(pyrrolidin-1-yl)-4-(trifluoromethyl)benzyl)piperazine-1-carboxylate to provide a solution comprising 1,1,1,3,3,3-hexafluoropropan-2-yl 4-(2-(pyrrolidin-1-yl)-4-(trifluoromethyl)benzyl)piperazine-1-carboxylate, optionally concentrating the solution.
  v) adding water to the solution comprising 1,1,1,3,3,3-hexafluoropropan-2-yl 4-(2-(pyrrolidin-1-yl)-4-(trifluoromethyl)benzyl)piperazine-1-carboxylate to form a suspension comprising 1,1,1,3,3,3-hexafluoropropan-2-yl 4-(2-(pyrrolidin-1-yl)-4-(trifluoromethyl)benzyl)piperazine-1-carboxylate.

E75. The process according to embodiment E74, wherein the $C_1$-$C_4$ alcohol is isopropanol or methanol.

E76. The process according to embodiments E74-E75, wherein the $C_1$-$C_4$ alcohol is methanol.

E77. The process according to embodiments E74-E76, wherein the $C_1$-$C_4$ alcohol is isopropanol.

E78. The process according to any one of embodiments E74-E77, wherein step c) further comprises the step of:
  vi) isolating 1,1,1,3,3,3-hexafluoropropan-2-yl 4-(2-(pyrrolidin-1-yl)-4-(trifluoromethyl)benzyl)piperazine-1-carboxylate from the suspension comprising 1,1,1,3,3,3-hexafluoropropan-2-yl 4-(2-(pyrrolidin-1-yl)-4-(trifluoromethyl)benzyl)piperazine-1-carboxylate obtained in step v).

E79. The process according to any one of embodiments E63-E78, wherein the acyl transfer agent in step a) is 1,1'-carbonyldiimidazole.

E80. The process according to embodiments E63-E79, wherein the first solvent in step a) is acetonitrile.

E81. The process according to any one of embodiments E63-E80, wherein the reducing agent in step c) is sodium triacetoxyborohydride.

E82. The process according to any one of embodiments E63-E81, wherein the organic base is triethylamine.

E83. The process according to any one of embodiments E63-E82, wherein 2-(pyrrolidin-1-yl)-4-(trifluoromethyl)benzaldehyde is obtained in step c0) prior to step c), wherein step c0) comprises the step of reacting 2-fluoro-4-(trifluoromethyl)benzaldehyde with pyrrolidine in the presence of a an inorganic base to form 2-(pyrrolidine-1-yl)-4-(trifluoromethyl)benzaldehyde, wherein the reaction in step c0) is carried out in ethyl acetate.

E84. The process according to any one of embodiments E63-E83, wherein the inorganic base is $Na_2CO_3$.

E85. The process according to any one of embodiments E46-E62, wherein the 1,1,1,3,3,3-hexafluoropropan-2-yl piperazine-1-carboxylate (A3), or a pharmaceutically acceptable salt thereof formed in step b) is obtained as 1,1,1,3,3,3-hexafluoropropan-2-yl piperazine-1-carboxylate mono-hydrochloride salt.

E86. The process according to anyone of embodiments E63-E84, wherein the compound 1,1,1,3,3,3-hexafluoropropan-2-yl piperazine-1-carboxylate, or a pharmaceutically acceptable salt thereof in step b) is obtained as 1,1,1,3,3,3-hexafluoropropan-2-yl piperazine-1-carboxylate monotrifluoroacetic acid.

E87. The process according to any of embodiments E1-E86, wherein 1,1,1,3,3,3-hexafluoropropan-2-yl 4-(2-(pyrrolidin-1-yl)-4-(trifluoromethyl)benzyl)piperazine-1-carboxylate is subsequently converted to 1,1,1,3,3,3-hexafluoropropan-2-yl 4-(2-(pyrrolidin-1-yl)-4-(trifluoromethyl)benzyl)piperazine-1-carboxylate mono-hydrochloride salt form 2.

E88. The process according to any one of embodiments E1-E86, wherein step c) is followed by step d) comprising:
  reacting 1,1,1,3,3,3-hexafluoropropan-2-yl 4-(2-(pyrrolidin-1-yl)-4-(trifluoromethyl)benzyl)piperazine-1-carboxylate with HCl in the presence of a fifth solvent to form crystalline 1,1,1,3,3,3-hexafluoropropan-2-yl 4-(2-(pyrrolidin-1-yl)-4-(trifluoromethyl)benzyl)piperazine-1-carboxylate mono-hydrochloride salt form 2.

E89. The process according to embodiment E88, wherein the fifth solvent is isopropanol.

E90. The process according to any one of embodiments E87-E89, wherein step d) further comprises the step of: isolating 1,1,1,3,3,3-hexafluoropropan-2-yl 4-(2-(pyrrolidin-1-yl)-4-(trifluoromethyl)benzyl)piperazine-1-carboxylate mono-hydrochloride salt form 2.

E91. A process for the manufacture of crystalline 1,1,1,3,3,3-hexafluoropropan-2-yl 4-(2-(pyrrolidin-1-yl)-4-(trifluoromethyl)benzyl)piperazine-1-carboxylate mono-hydrochloride salt form 2 comprising the steps of:
  manufacturing 1,1,1,3,3,3-hexafluoropropan-2-yl 4-(2-(pyrrolidin-1-yl)-4-(trifluoromethyl)benzyl)piperazine-1-carboxylate by the process according to any one of embodiments E1-E85, and
  d) converting 1,1,1,3,3,3-hexafluoropropan-2-yl 4-(2-(pyrrolidin-1-yl)-4-(trifluoromethyl)benzyl)piperazine-1-carboxylate to crystalline 1,1,1,3,3,3-hexafluoropropan-2-yl 4-(2-(pyrrolidin-1-yl)-4-(trifluoromethyl)benzyl)piperazine-1-carboxylate mono-hydrochloride salt form 2.

E92. The process according to embodiment E91, wherein step d) comprises the steps of reacting 1,1,1,3,3,3-hexafluoropropan-2-yl 4-(2-(pyrrolidin-1-yl)-4-(trifluoromethyl)benzyl)piperazine-1-carboxylate with HCl in the presence of a fifth solvent to form crystalline 1,1,1,3,3,3-hexafluoropropan-2-yl 4-(2-(pyrrolidin-1-yl)-4-(trifluoromethyl)benzyl)piperazine-1-carboxylate mono-hydrochloride salt form 2.

E93. The process according to embodiment E92, wherein the fifth solvent is isopropanol.

E94. The process according to any one of embodiments E82-E88, wherein the obtained 1,1,1,3,3,3-hexafluoropropan-2-yl 4-(2-(pyrrolidin-1-yl)-4-(trifluoromethyl)benzyl)piperazine-1-carboxylate mono-hydrochloride salt is 1,1,1,3,3,3-hexafluoropropan-2-yl 4-(2-(pyrrolidin-1-yl)-4-(trifluoromethyl)benzyl)piperazine-1-carboxylate mono-hydrochloride salt form 2 identifiable by an X-ray powder diffraction (XRPD) pattern with characteristic peaks at 8.6° 2-Theta, 14.3° 2-Theta, 15.6° 2-Theta, 19.0° 2-Theta, 19.8° 2-Theta, and 20.7° 2-Theta.

E95. The process according to any one of embodiments E87-E90, wherein step d) is carried out in the presence of a seed crystal of 1,1,1,3,3,3-hexafluoropropan-2-yl 4-(2-(pyrrolidin-1-yl)-4-(trifluoromethyl)benzyl)piperazine-1-carboxylate mono-hydrochloride salt form 2.

E96. The process according to any one of embodiments E87-E95, wherein the obtained crystalline 1,1,1,3,3,3-hexafluoropropan-2-yl 4-(2-(pyrrolidin-1-yl)-4-(trifluoromethyl)benzyl)piperazine-1-carboxylate mono-hydrochloride form 2 is characterized by having an X-ray powder diffraction (XRPD) pattern with characteristic peaks at 8.6° 2-Theta, 14.3° 2-Theta, 15.6° 2-Theta, 19.0° 2-Theta, 19.8° 2-Theta, and 20.7° 2-Theta.

E97. A process for the manufacture of crystalline 1,1,1,3,3,3-hexafluoropropan-2-yl 4-(2-(pyrrolidin-1-yl)-4-(trifluoromethyl)benzyl)piperazine-1-carboxylate mono-hydrochloride salt form 2 comprising the steps of:

D1) dissolving 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof in a sixth solvent at a temperature of 38-70° C., preferably at a temperature of 38-42° C., optionally under stirring;

D2) converting the 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof into 1,1,1,3,3,3-hexafluoropropan-2-yl 4-(2-(pyrrolidin-1-yl)-4-(trifluoromethyl)benzyl)piperazine-1-carboxylate mono-hydrochloride salt by addition of HCl, optionally under stirring at a temperature of 70-76° C., preferably at a temperature of 74-76° C.;

D3) optionally filtering the solution obtained in step D2)

D4) cooling the resulting solution obtained in step D2) to 63-69° C., preferably to 65-68° C., and adding seed crystals of 1,1,1,3,3,3-hexafluoropropan-2-yl 4-(2-(pyrrolidin-1-yl)-4-(trifluoromethyl)benzyl)piperazine-1-carboxylate mono-hydrochloride salt form 2;

D5) optionally, stirring the obtained suspension from step D4) for at least 1 hour;

D6) cooling the suspension from 63-69° C. to a temperature of 10-40° C., preferably at a temperature of 16-23° C. during a period between 12-20 hours under stirring.

Surprisingly the inventors found that by the present method it was possible to control the crystallization of 1,1,1,3,3,3-hexafluoropropan-2-yl 4-(2-(pyrrolidin-1-yl)-4-(trifluoromethyl)benzyl)piperazine-1-carboxylate mono-hydrochloride salt form 2 having high purity, high yield and having a PSD suitable for further preparation of a solid dosage form such as a tablet.

E98. The process according to embodiment E97, wherein the process further comprises a step D7) of isolating the wet cake of crystalline 1,1,1,3,3,3-hexafluoropropan-2-yl 4-(2-(pyrrolidin-1-yl)-4-(trifluoromethyl)benzyl)piperazine-1-carboxylate mono-hydrochloride salt form 2.

E99. The process according to any one of embodiments E97-E98, wherein the process further comprises a step D8) of washing the wet cake of crystalline 1,1,1,3,3,3-hexafluoropropan-2-yl 4-(2-(pyrrolidin-1-yl)-4-(trifluoromethyl)benzyl)piperazine-1-carboxylate mono-hydrochloride salt form 2, preferably the wash is performed with the sixth solvent as used in step D1.

E100. The process according to any one of embodiments E97-E99, wherein the process comprises a further step D9) of drying the wet solid to provide dry crystalline 1,1,1,3,3,3-hexafluoropropan-2-yl 4-(2-(pyrrolidin-1-yl)-4-(trifluoromethyl)benzyl)piperazine-1-carboxylate mono-hydrochloride salt form 2.

E101. The process according to any one of embodiments E97-E100, wherein the process comprising a further step of isolating 1,1,1,3,3,3-hexafluoropropan-2-yl 4-(2-(pyrrolidin-1-yl)-4-(trifluoromethyl)benzyl)piperazine-1-carboxylate mono-hydrochloride salt form 2.

E102. The process according to any one of embodiments E97-E101, wherein the sixth solvent is a $C_1$-$C_4$ alcohol, preferably the sixth solvent is isopropanol.

E103. The process according to any one of embodiments E97-102, wherein the seed crystals is characterized by having a d10 particle size of 10-30 μm; a d90 particle size below 200 μm, optionally a d50 particle size ranging of 60-80 μm, optionally the seed crystal is milled.

E104. The process according to any one of embodiments E97-E103, wherein the wet solid is dried at a temperature of 30-45° C. for 6-10 hours.

E105. The process according to any one of embodiments E97-E104, wherein step D6) comprises the steps of:

Cooling the suspension from 63-69° C. to 61-64° C. in approximately 2 hours and stirring the suspension for 2 hours at 61-63° C., then cooling the suspension to 51-53° C. in approximately 2 hours, then cooling the suspension to 36-38° C. in approx. 2 hours, then cooling the suspension to 18-20° C. in approximately 2 hours and stirring the suspension at 18-20° C. for further 6 hours.

E106. The process according to any one of embodiments E97-E105, wherein the process further comprises the step of milling the obtained crystalline 1,1,1,3,3,3-hexafluoropropan-2-yl 4-(2-(pyrrolidin-1-yl)-4-(trifluoromethyl)benzyl)piperazine-1-carboxylate mono-hydrochloride salt form 2, preferably via a hammer mill.

E107. The process according to any one of embodiments E97-E106, wherein crystalline 1,1,1,3,3,3-hexafluoropropan-2-yl 4-(2-(pyrrolidin-1-yl)-4-(trifluoromethyl)benzyl)piperazine-1-carboxylate mono-hydrochloride salt form 2 is characterized by having a d10 particle size of 10-30 μm; a d90 particle size ranging below 200 μm, optionally a d50 particle size ranging of 60-80 μm.

E108. The process according to any one of embodiments E97-E107, wherein crystalline 1,1,1,3,3,3-hexaluoropropan-2-yl 4-(2-(pyrrolidin-1-yl)-4-(trifluoromethyl)benzyl)piperazine-1-carboxylate mono-hydrochloride salt form 2 is formulated into a solid dosage form.

E109. The process according to embodiment E108, wherein the crystalline 1,1,1,3,3,3-hexafluoropropan-2-yl 4-(2-(pyrrolidin-1-yl)-4-(trifluoromethyl)benzyl)piperazine-1-carboxylate mono-hydrochloride salt form 2 is formulated into a tablet.

E110. The process according to any one of embodiments E97-E109, wherein the obtained crystalline 1,1,1,3,3,3-hexafluoropropan-2-yl 4-(2-(pyrrolidin-1-yl)-4-(trifluoromethyl)benzyl)piperazine-1-carboxylate mono-hydrochloride form 2 is characterized by having an X-ray powder diffraction (XRPD) pattern with characteristic peaks at 8.6° 2-Theta, 14.3° 2-Theta, 15.6° 2-Theta, 19.0° 2-Theta, 19.8° 2-Theta, and 20.7° 2-Theta.

E111. A process for the manufacture of crystalline 1,1,1,3,3,3-hexafluoropropan-2-yl 4-(2-(pyrrolidin-1-yl)-4-(trifluoromethyl)benzyl)piperazine-1-carboxylate mono-hydrochloride form 2 comprising the steps of:

Providing 1,1,1,3,3,3-hexafluoropropan-2-yl 4-(2-(pyrrolidin-1-yl)-4-(trifluoromethyl)benzyl)piperazine-1-carboxylate according to any one of embodiments E1-E86

Converting 1,1,1,3,3,3-hexafluoropropan-2-yl 4-(2-(pyrrolidin-1-yl)-4-(trifluoromethyl)benzyl)piperazine-1-carboxylate to crystalline 1,1,1,3,3,3-hexafluoropropan-2-yl 4-(2-(pyrrolidin-1-yl)-4-(trifluoromethyl)benzyl)piperazine-1-carboxylate mono-hydrochloride form 2 according to any one of embodiments E96-E108.

E112. Use of crystalline 1,1,1,3,3,3-hexafluoropropan-2-yl 4-(2-(pyrrolidin-1-yl)-4-(trifluoromethyl)benzyl)piperazine-1-carboxylate mono-hydrochloride salt form 2 particles for the preparation of a solid dosage form comprising 1,1,1,3,3,3-hexafluoropropan-2-yl 4-(2-(pyrrolidin-1-yl)-4-(trifluoromethyl)benzyl)piperazine-1-carboxylate mono-hydrochloride salt form 2, wherein the particle size distribution of crystalline 1,1,1,3,3,3-hexafluoropropan-2-yl 4-(2-(pyrrolidin-1-yl)-4-(trifluoromethyl)benzyl)piperazine-1-carboxylate mono-hydrochloride salt form 2 is characterized by having a d10 particle size of 10-30 µm; a d90 particle size ranging below 200 µm, optionally a d50 particle size ranging of 60-80 am, wherein the crystalline 1,1,1,3,3,3-hexafluoropropan-2-yl 4-(2-(pyrrolidin-1-yl)-4-(trifluoromethyl)benzyl)piperazine-1-carboxylate mono-hydrochloride form 2 is characterized by having an X-ray powder diffraction (XRPD) pattern with characteristic peaks at 8.6° 2-Theta, 14.3° 2-Theta, 15.6° 2-Theta, 19.0° 2-Theta, 19.8° 2-Theta, and 20.7° 2-Theta.

E113. 1,1,1,3,3,3-hexafluoropropan-2-yl piperazine-1-carboxylate mono-hydrochloride salt.

Item List

In the following, various items of the invention are disclosed. The first item is denoted item 1, the second item is denoted item 2 and so forth.

Item 1. A process for the manufacture of 1,1,1,3,3,3-hexafluoropropan-2-yl 4-(2-(pyrrolidine-1-yl)-4-(trifluoromethyl)benzyl)piperazine-1-carboxylate comprising the steps of:
   a) reacting tert-butyl piperazine-1-carboxylate (A1) with hexafluoropropan-2-ol in the presence of an acyl transfer agent to form 1-(tert-butyl) 4-(1,1,1,3,3,3-hexafluoropropan-2-yl) piperazine-1,4-dicarboxylate (A2), wherein step a) is carried out in a first solvent;
   b) reacting 1-(tert-butyl) 4-(1,1,1,3,3,3-hexafluoropropan-2-yl) piperazine-1,4-dicarboxylate (A2) obtained in step a) with a strong acid to form 1,1,1,3,3,3-hexafluoropropan-2-yl piperazine-1-carboxylate (A3), or a pharmaceutically acceptable salt thereof, wherein step b) is optionally carried out in a second solvent;
   c) reacting 1,1,1,3,3,3-hexafluoropropan-2-yl piperazine-1-carboxylate (A3), or a pharmaceutically acceptable salt thereof obtained in step b) with 2-(pyrrolidine-1-yl)-4-(trifluoromethyl)benzaldehyde in the presence of a reducing agent and an organic base to form a reaction mixture comprising 1,1,1,3,3,3-hexafluoropropan-2-yl 4-(2-(pyrrolidine-1-yl)-4-(trifluoromethyl)benzyl)piperazine-1-carboxylate, wherein the reaction in step c) is carried out in a third solvent.

Item 2. The process according to item 1, wherein step a) is carried out under pressure of 2 bar 10 to 6 bar.

Item 3. The process according to any one of items 1-2, wherein the ingredients in step a) are added in the consecutive order of the acyl transfer agent, the first solvent, tert-butyl piperazine-1-carboxylate (A1), and hexafluoropropan-2-ol.

Item 4. The process according to any one of items 1-3, wherein the first solvent is an aprotic solvent.

Item 5. The process according to any one of items 1-4, wherein the strong acid in step b) is trifluoroacetic acid or HCl.

Item 6. The process according to any one of items 1-5, wherein the strong acid in step b) is trifluoroacetic acid, and the ingredients in step b) are added in the consecutive order of trifluoroacetic acid followed by 1-(tert-butyl) 4-(1,1,1,3,3,3-hexafluoropropan-2-yl) piperazine-1,4-dicarboxylate (A2) to form a mixture comprising 1,1,1,3,3,3-hexafluoropropan-2-yl piperazine-1-carboxylate (A3), or a pharmaceutically acceptable salt thereof and trifluoroacetic acid.

Item 7. The process according to item 6, wherein 1-(tert-butyl) 4-(1,1,1,3,3,3-hexafluoropropan-2-yl) piperazine-1,4-dicarboxylate (A2) in step b) is added to trifluoroacetic acid at around 10-30° C. to provide the mixture comprising 1,1,1,3,3,3-hexafluoropropan-2-yl piperazine-1-carboxylate (A3), or a pharmaceutically acceptable salt thereof and trifluoroacetic acid.

Item 8. The process according to any one of items 6-7, wherein step b) comprises a step comprising: adding water to the mixture comprising 1,1,1,3,3,3-hexafluoropropan-2-yl piperazine-1-carboxylate (A3), or a pharmaceutically acceptable salt thereof and trifluoroacetic acid to form a suspension.

Item 9. The process according to item 8, wherein the water is added at 35-50° C.

Item 10. The process according to any one of items 1-5, wherein the strong acid in step b) is HCl; and wherein the step b) is carried out in a second solvent.

Item 11. The process according to item 10, wherein the second solvent is selected from the group consisting of toluene, isopropyl acetate, dichloromethane, acetonitrile, ethers and esters.

Item 12. The process according to any one of items 1-11, wherein the third solvent in step c) is ethyl acetate.

Item 13. The process according to any one of items 1-12, wherein the reducing agent in step c) is sodium triacetoxyborohydride, $H_2$ in the presence of Pd/C, $H_2$ in the presence of Rh/C, and sodium cyanoborohydride.

Item 14. The process according to any one of items 1-13, wherein the organic base in step c) is selected from the group consisting of triethylamine, N,N-diisopropylethylamine, pyridine, and 2,6-lutidine.

Item 15. The process according to any one of items 1-14, wherein step c) comprises the steps of:
   i) providing a mixture comprising 1,1,1,3,3,3-hexafluoropropan-2-yl piperazine-1-carboxylate (A3), or a pharmaceutically acceptable salt thereof obtained in step b), 2-(pyrrolidine-1-yl)-4-(trifluoromethyl)benzaldehyde, the organic base, and the third solvent;
   ii) adding the reducing agent to the mixture obtained from step i) to provide the reaction mixture comprising 1,1,1,3,3,3-hexafluoropropan-2-yl 4-(2-(pyrrolidine-1-yl)-4-(trifluoromethyl)benzyl)piperazine-1-carboxylate.

Item 16. The process according to any one of items 1-15, wherein step c) further comprises the step of:
   iii) adding water to the reaction mixture comprising 1,1,1,3,3,3-hexafluoropropan-2-yl 4-(2-(pyrrolidine-1-yl)-4-(trifluoromethyl)benzyl)piperazine-1-carboxylate to form a phase separation having an organic phase comprising 1,1,1,3,3,3-hexafluoropropan-2-yl 4-(2-(pyrrolidine-1-yl)-4-(trifluoromethyl)benzyl)piperazine-1-carboxylate, followed by diluting the organic phase with the third solvent.

Item 17. The process according to item 16, wherein step c) further comprises the steps of:
   iv) adding an $C_1$-$C_4$ alcohol to the organic phase comprising 1,1,1,3,3,3-hexafluoropropan-2-yl 4-(2-(pyrrolidine-1-yl)-4-(trifluoromethyl)benzyl)piperazine-1-carboxylate to provide a solution comprising 1,1,1,3,3,3-hexafluoropropan-2-yl 4-(2-(pyrrolidine-1-yl)-4-(trifluoromethyl)benzyl)piperazine-1-carboxylate, optionally concentrating the solution.
   v) adding water to the solution comprising 1,1,1,3,3,3-hexafluoropropan-2-yl 4-(2-(pyrrolidine-1-yl)-4-(trifluoromethyl)benzyl)piperazine-1-carboxylate to form a suspension comprising 1,1,1,3,3,3-hexafluoropropan-2-yl 4-(2-(pyrrolidine-1-yl)-4-(trifluoromethyl)benzyl)piperazine-1-carboxylate.

Item 18. The process according to item 17, wherein step c) further comprises the step of:

vi) isolating 1,1,1,3,3,3-hexafluoropropan-2-yl 4-(2-(pyrrolidine-1-yl)-4-(trifluoromethyl)benzyl)piperazine-1-carboxylate from the suspension comprising 1,1,1,3,3,3-hexafluoropropan-2-yl 4-(2-(pyrrolidine-1-yl)-4-(trifluoromethyl)benzyl)piperazine-1-carboxylate obtained in item 1.

Item 19. The process according to any one of items 1-18, wherein 2-(pyrrolidine-1-yl)-4-(trifluoromethyl)benzaldehyde is obtained in step c0) prior to step c), wherein step c0) comprises the step of; reacting 2-fluoro-4-(trifluoromethyl)benzaldehyde with pyrrolidine in the presence of an inorganic base to form 2-(pyrrolidine-1-yl)-4-(trifluoromethyl)benzaldehyde, wherein the reaction in step c0) is carried out in the fourth solvent.

Item 20. The process according to item 19, wherein the inorganic base and the fourth solvent in step c0) is $Na_2CO_3$ and ethyl acetate.

Item 21. A process for the manufacture of 1,1,1,3,3,3-hexafluoropropan-2-yl 4-(2-(pyrrolidine-1-yl)-4-(trifluoromethyl)benzyl)piperazine-1-carboxylate mono-hydrochloride salt comprising the steps of:
manufacturing 1,1,1,3,3,3-hexafluoropropan-2-yl 4-(2-(pyrrolidine-1-yl)-4-(trifluoromethyl)benzyl)piperazine-1-carboxylate by the process according to any one of items 1-20, and
d) Converting 1,1,1,3,3,3-hexafluoropropan-2-yl 4-(2-(pyrrolidine-1-yl)-4-(trifluoromethyl)benzyl)piperazine-1-carboxylate to 1,1,1,3,3,3-hexafluoropropan-2-yl 4-(2-(pyrrolidine-1-yl)-4-(trifluoromethyl)benzyl)piperazine-1-carboxylate mono-hydrochloride salt form 2.

Item 22. The process according to item 22, wherein step d) comprises the steps of: reacting 1,1,1,3,3,3-hexafluoropropan-2-yl 4-(2-(pyrrolidin-1-yl)-4-(trifluoromethyl)benzyl)piperazine-1-carboxylate with HCl in the presence of a fifth solvent to form crystalline 1,1,1,3,3,3-hexafluoropropan-2-yl 4-(2-(pyrrolidin-1-yl)-4-(trifluoromethyl)benzyl)piperazine-1-carboxylate mono-hydrochloride salt form 2.

Item 23. The process according to item 22, wherein the fifth solvent is isopropanol.

Item 24. The process according to any one of items 21-23, wherein the obtained 1,1,1,3,3,3-hexafluoropropan-2-yl 4-(2-(pyrrolidin-1-yl)-4-(trifluoromethyl)benzyl)piperazine-1-carboxylate mono-hydrochloride salt form 2 is characterized by an X-ray powder diffraction (XRPD) pattern with characteristic peaks at 8.6° 2-Theta, 14.3° 2-Theta, 15.6° 2-Theta, 19.0° 2-Theta, 19.8° 2-Theta, and 20.7° 2-Theta.

EXPERIMENTAL SECTION

General Methods $^1$H-NMR spectrum was recorded at 20° C. on a Bruker Advance III HD 400 NMR operating at 400 MHz for 1H using 5 mm diameter NMR tubes.

The Chemical Shifts are reported and calculated against the residual not deuterated solvent. The following abbreviations are used for NMR data: s, singlet; bs, broad singlet; d, doublet; t, triplet; q, quartet; m, multiplet.

MS spectrum was recorded using an Agilent 6310 Ion Trap

List Of Abbreviations

As used above, and throughout the description of the invention, the following abbreviations, unless otherwise indicated, shall be understood to have the following meanings:

TFA trifluoroacetic acid
CDI 1,1'-carbonyldiimidazole
ACN acetonitrile
iPrOAc isopropyl acetate
EtOAc ethyl acetate
TEA triethylamine
STAB Sodium triacetoxyborohydride
NMT no more than
THF tetrahydrofuran Chemical Synthesis Unless otherwise noted, reagents and solvents were used as received from commercial suppliers.

Example 1: Synthesis of A2

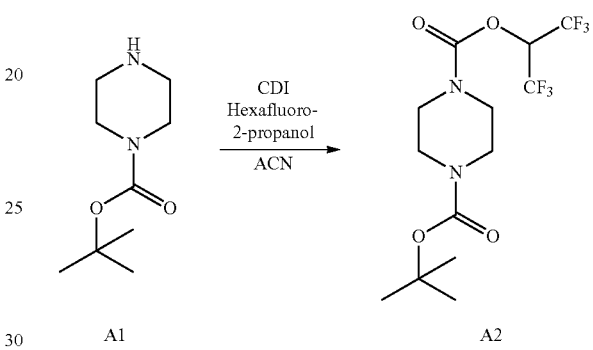

Step a): CDI (62 kg) and A1 (68 kg) were charged in a vessel followed by acetonitrile as solvent (214 kg) and stirred at 20-25° C. for around 4 hours. Hexafluoropropan-2-ol (117 kg) was added over a period of 34 minutes in the temperature range of 5–12° C. then the solution was pressurized to 2 bar, followed by heating the solution to 98-102° C. (internal pressure reached 4 bar) and stirred for around 15 hours. Hexafluoropropan-2-ol (6 kg) was added and stirred for an additional 12 hours at 4 bar.

The solution was then cooled to a temperature of 36-38° C., purified water (204 kg) was added over 30 minutes while maintaining the temperature in the range of 35–40° C. ACN was removed by distillation below 40° C. under vacuum then purified water (476 kg) was added over a period of 20 minutes while maintaining the temperature below 38° C. The suspension was stirred for 2 hours at 24-25° C. and the product was isolated and washed with purified water over two cycles (first wash 136 kg, and second wash 680 kg). The suspension was stirred at 22-25° C. for around 1 hour and the product was isolated and washed with purified water (340 kg). The product was finally dried under vacuum at 30-32° C. for a minimum of 8 hours to afford A2 (127 kg, yield 91.5%). $^1$H-NMR (DMSO-$d_6$): δ(ppm) 1.40 (9H, s), 3.34-3.44 (8H, m), 6.58-6.64 (1H, m).

Optional Re-Work Procedure of A2

Starting A2 (25 kg), was suspended in a water/acetonitrile mixture (125 kg/98.2 kg) and the suspension was stirred for about 3 hours at 23-24° C. in a vessel then A2 was isolated and washed with a water/ACN mixture (25 kg/19.6 kg). The product was finally dried under vacuum at 35-40° C. for a minimum of 8 hours to afford A2 (23.73 kg, yield 94.9%). ¹H NMR correspond to ¹H NMR obtained above.

Example 2: Alternative Synthesis of A2

Step a): CDI (86.5 kg) was charged in a vessel followed by acetonitrile as solvent (282 kg) and finally A1 (90 kg) then stirred at 20-25° C. for around 3-4 hours. Hexafluoropropan-2-ol (155 kg) was added over a period of 1 hour in the temperature range of 5-12° C., then the solution was pressurized to 2 bar, followed by heating the solution to 98-102° C. (internal pressure reached 4 bar) and stirred for around 15 hours. Hexafluoropropan-2-ol (8 kg) was added and stirred for an additional 4 hours at 4 bar.

The solution was then cooled to a temperature of 36-38° C., purified water (271 kg) was added over 50 minutes while maintaining the temperature in the range of 35-40° C. ACN was removed by distillation below 40° C. under vacuum then purified water (631 kg) was added over a period of 75 minutes while maintaining the temperature below 38° C. The suspension was stirred for 3 hours at 22-25° C. and the product was isolated and washed with purified water over two cycles (first wash 180 kg, and second wash 900 kg). The suspension was stirred at 22-25° C. for around 2 hours and the product was isolated and washed with purified water (450 kg). The product was finally dried under vacuum at 30-32° C. for a minimum of 8 hours to afford A2 (164 kg, yield 89.2%)

Example 3: Synthesis of A3 Via TFA Route

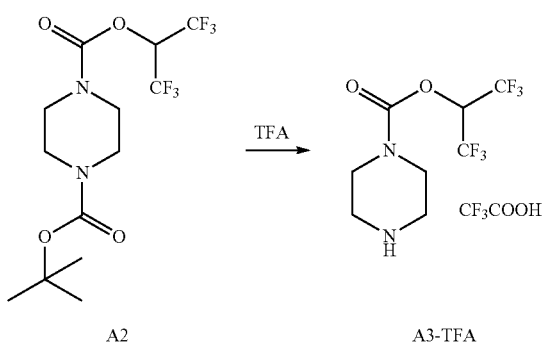

Step b) via TFA route: Trifluoroacetic acid TFA (150 kg) was charged in a vessel at 15-27° C. followed by addition of A2 (100 kg) over 5 hours to control gas evolution. The reaction mixture was stirred at 25° C. for 2 hours, followed by heating the reaction mixture heated to 40-45° C., and purified water (1000 kg) was then added over 2 hours and 15 minutes. The obtained suspension was cooled to 3-7° C. over 7 hours and 45 minutes then centrifuged and washed with purified water (100 kg). The wet solid was dried under vacuum at 35-40° C. for 12 hours affording the dry product A3-TFA (96.31 kg, yield 92.9%). ¹H-NMR (DMSO-d₆): δ(ppm) 3.16-3.20 (4H, m), 3.66 (4H, m), 6.59-6.69 (1H, m), 9.25 (1H, s).

Example 4: Synthesis of A3 Via HCl Route

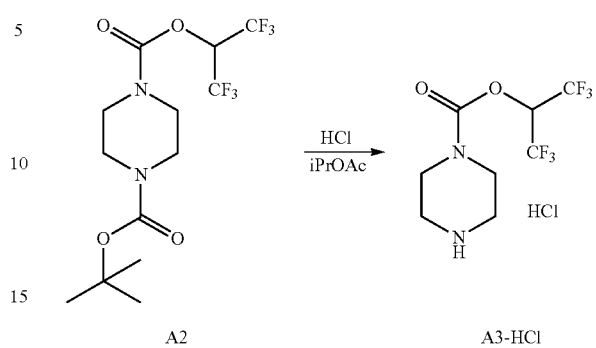

Step b) via HCl route: A2 (23.73 kg) was charged in a vessel followed by iPrOAc (62.2 kg) obtaining a suspension/partial dissolution of the solid. A solution approx. 12% of HCl in iPrOAc (approx. 70 kg) was added at 15-23° C. over 1 hour while observing initial dissolution followed by crystallization of the product. Subsequently, the suspension was stirred at 25° C. for 2 hours then heated to 60° C. over 2 hours, followed by stirring at 60° C. for 4 hours. Subsequently, the suspension was cooled to 40° C. Afterwards, the suspension was cooled to 10° C. over 1 hour and 30 minutes and stirred at 10° C. for 2 hours. The product was isolated and washed two times with iPrOAc (10.4 kg in each wash) and dried at 35-40° C. for 11 hours affording the dry product A3-HCl (19.06 kg, yield 96.5%). ¹H-NMR (DMSO-d₆): δ(ppm) 3.14-3.150 (4H, m), 3.70 (4H, bs), 6.57-6.67 (1H, m), 9.57 (1H, s).

Example 5

Alternative Synthesis of A3 Via HCl Route:

Step b) via HCl route: A2 (164 kg) was charged in a vessel followed by iPrOAc (858 kg) obtaining a suspension/partial dissolution of the solid. Gaseous HCl (approx. 75 kg) was bubbled at 20-25° C. over 7 hours. Subsequently, the suspension was stirred at 20-25° C. for 30 minutes then heated to 60° C. over 5 hours, followed by stirring at 60° C. for few minutes. Afterwards, the suspension was cooled to 8-12° C. over 3 hours and stirred at 8-12° C. for 8 hours. the product was isolated and washed two times with iPrOAc (66.5 kg in each wash) and dried at about 35-40° C. for 13 hours affording the dry product A3-HCl (130.29 kg, yield 95.2%)

Example 6: Synthesis of A5 Via Sodium Carbonate

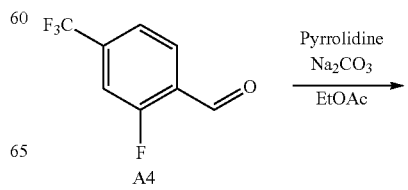

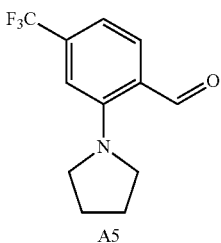

A5

Step c0) via sodium carbonate: Sodium carbonate (12.5 kg) and EtOAc (56.3 kg) were charged in vessel that was then inerted with nitrogen/vacuum cycles. A4 (15 kg) was charged under nitrogen followed by washing the charging line with Ethyl acetate (5.6 kg). Subsequently, pyrrolidine (5.6 kg) was added to the reaction mixture under nitrogen at 20° C., followed by another wash of the charging line with Ethyl acetate (5.6 kg). The reaction mixture was heated to around 77° C. and stirred vigorously at 77° C. for 12.5 hours. Reaction mixture was cooled to 20-23° C. and purified water (120 kg,) was added. After mixing, phases were separated. The organic phase was washed with purified water (120 kg) and distilled under vacuum affording a solution (41 kg) with a content of A5 of around 44 wt %.

Example 7

Alternative Synthesis of A5 Via Sodium Carbonate

Sodium carbonate (31 kg) and EtOAc (140 kg) were charged in vessel that was then inerted with nitrogen/vacuum cycles. A4 (37.5 kg) was charged under nitrogen followed by washing the charging line with Ethyl acetate (19 kg). Subsequently, pyrrolidine (14 kg) was added to the reaction mixture under nitrogen at 20° C., followed by another wash of the charging line with Ethyl acetate (14 kg). The reaction mixture was heated to around 77° C. and stirred vigorously at 77° C. for 14 hours. Reaction mixture was cooled to 20-25° C. and purified water (300 kg,) was added. After mixing, phases were separated. The organic phase was washed with purified water (300 kg) and distilled under vacuum affording a solution (approx. 100 kg) with a content of A5 of around 45 wt %. Water (1.1 kg) was added to reach a water content of approx. 1% w/w.

Example 8: Synthesis of A5 Via Sodium Bicarbonate

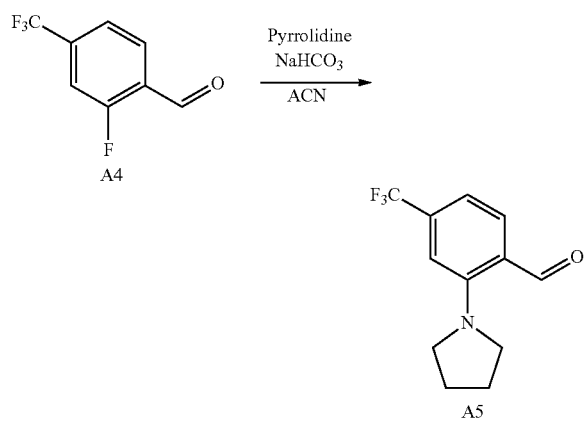

Step c0) via sodium bicarbonate: A4 (8 kg) was charged in a vessel followed by ACN as solvent (31.4 kg), pyrrolidine (2.96 kg) and sodium bicarbonate (8.75 kg) at 13-23° C. Reaction mixture was heated to 73-74° C. and stirred at this temperature for 5-7 hours. Subsequently, the reaction mixture was cooled to 18-22° C. and purified water (80 kg) was added. Solvents (ACN/water) were distilled under vacuum, followed by addition of EtOAc (35.9 kg) and stirring at 30-40° C. providing a phase separation. The aqueous phase was back-extracted with EtOAc (35.9 kg) and the organic phases collected together. Then organics were washed with brine (solution made of NaCl 4.9 kg/purified water 14.6 kg) and distilled to dryness to remove EtOAc. Finally, THF (94.2 kg) was added and mixed to obtain a THF solution (100 kg) of A5 (10 kg, 10 wt. %).

Example 9: Synthesis of Compound I Via TFA Route

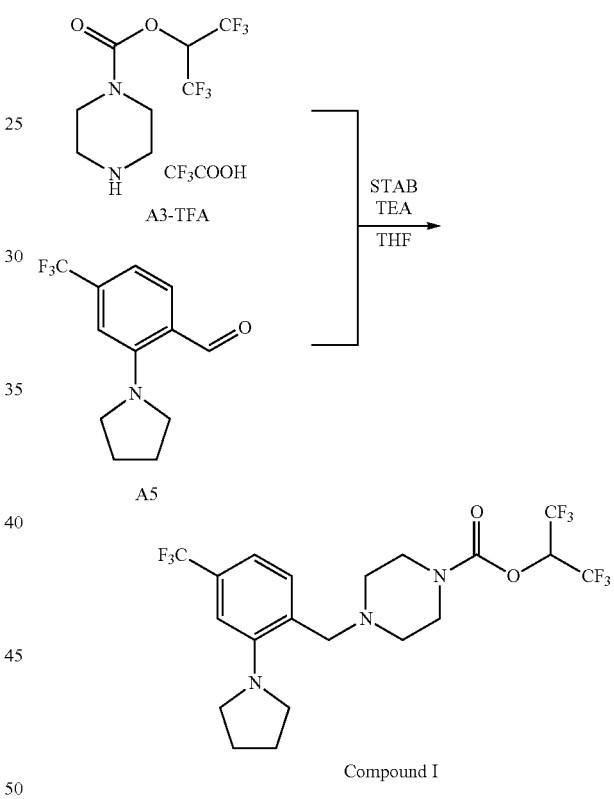

Compound I

Step c) via TFA route: A3-TFA (16.2 kg) was charged in a vessel at 20-25° C. followed by EtOAc (57 kg) at 20-25° C. obtaining a suspension. TEA (4.4 kg) was added over 15 min and the mixture was stirred at 20-25° C. for 1 hour. The A5 solution obtained in example 5 (20.5 kg) was added under nitrogen over 15 min at 20-25° C. and the mixture was stirred at 20-25° C. for 3 hours. STAB (9.8 kg) was added in 4 equal portions, waiting about 30 minutes between every portion and the following one while maintaining the temperature between 20 and 25° C. Subsequently, the suspension was stirred for 12 hours, followed by the addition of a further portion of STAB (1.4 kg) and a further stirring period of 2 hours. Subsequently, a further portion of STAB (0.3 kg) was added to the suspension followed by stirring for 2 hours.

Purified water (13.5 kg) was added at 20° C. over 2 hours to form a phase separation. The organic phase was diluted with EtOAc (12.3 kg) and washed with purified water (63.2 kg). The organic phase was concentrated under vacuum below 40° C. to approx. 25 l. Methanol (21.4 kg) was added and solution was concentrated under vacuum to approx. 25 l. Methanol (48.2 kg) was added and the solution heated to 48-52° C. Purified water (81.2 kg) was slowly added in approx. 2 hours obtaining a suspension that was stirred at 48-52° C. for 30 minutes, followed by cooling to 20° C. over 3 hours and stirred at 20° C. for 3 hours. Suspension was centrifugated and washed with purified water/methanol mixture (27.1 kg/47.6 kg), the wet solid (18.49 kg) was dried under nitrogen flow for no less than 8 hours in a static drier affording Compound 1 (17.29 kg, 92% yield). $^1$H-NMR (DMSO-d$_6$): δ(ppm) 1.86-1.89 (4H, t), 2.39 (4H, m), 3.24-3.27 (4H, t), 3.56 (2H, s), 6.53-6.63 (1H, m), 7.01-7.02 (1H, d), 7.09-7.11 (1H, dd), 7.53-7.55 (1H, d).

Example 10: Synthesis of Compound I Via HCl Route

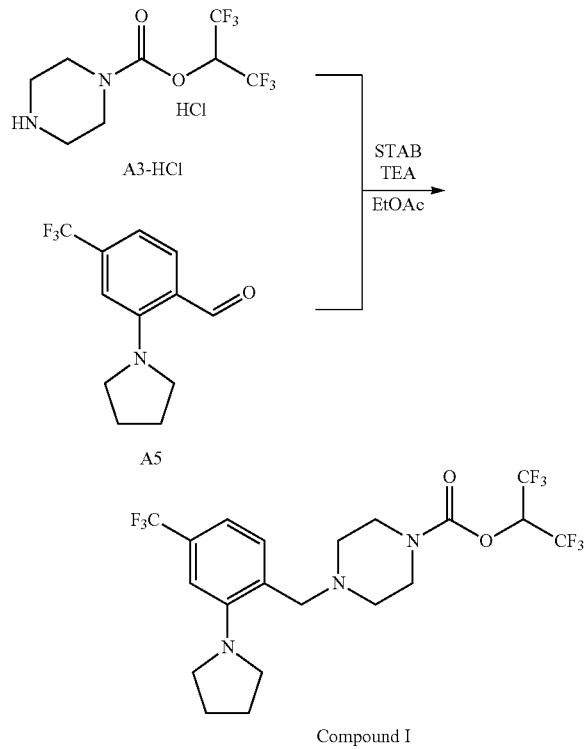

Step c) via HCl route: A3-HCl (12.9 kg, 1.43 wt. %) was charged in vessel at 20-25° C. followed by EtOAc (57 kg) at 20-25° C. obtaining a suspension. TEA (4.4 kg) was added over 15 min and the mixture was stirred at 20-25° C. for 1 hour. Water (102 g) was added to the A5 solution from example 4 (20.5 kg at 44% w/w).

The A5 solution was then added under nitrogen over 15 min at 20-25° C. and the mixture was stirred at 20-25° C. for 3 hours. STAB (9.8 kg) was added in 4 equal portions waiting about 30 minutes between every portion and the following one while maintaining the temperature between 20-25° C. The suspension was stirred for 15 hours. Purified water (13.5 kg) was added at 20° C. over 2 hours to obtain a phase separation. The organic phase was diluted with EtOAc (12.3 kg) and washed with purified water (63.2 kg). The organic phase was concentrated under vacuum below 40° C. to approx. 25 l. Methanol (21.4 kg) was added and solution was concentrated again under vacuum to approx. (25 l). Methanol (48.2 kg) was added and the solution was heated to 48-52° C. Purified water (81.2 kg) was slowly added over approx. 2 hours obtaining a suspension that was stirred at 48-52° C. for 30 minutes then cooled to 20° C. over 3 hours and stirred at 20° C. for approx. 3 hours. Suspension was centrifugated and washed with a purified water/methanol mixture (27.1 kg/47.6 kg). The wet solid (18.33 kg) was dried under nitrogen flow in a static drier for about 8 hours affording Compound 1 (17.33 kg, yield 92%). $^1$H-NMR (DMSO-d$_6$): δ(ppm) 1.86-1.89 (4H, t), 2.39 (4H, m), 3.24-3.27 (4H, t), 3.56 (2H, s), 6.53-6.63 (1H, m), 7.01-7.02 (1H, d), 7.09-7.11 (1H, dd), 7.53-7.55 (1H, d).

Example 11: Alternative Synthesis of Compound I Via HCl Route

Step c) via HCl route: A3-HCl (64.45 kg) was charged in vessel at 20-25° C. followed by EtOAc (250 kg) at 20-25° C. obtaining a suspension. TEA (22.5 kg) was added over 15 min and the mixture was stirred at 20-25° C. for 1.5 hours.

The A5 solution (approx. 100 kg) was then added under nitrogen over 15 min followed by a rinse of EtOAc (20 kg) at 20-25° C. and the mixture was stirred at 20-25° C. for 3 hours. STAB (54.9 kg) was added in 4 equal portions waiting about 60 minutes between every portion and the following one while maintaining the temperature between 20-25° C. The suspension was stirred for 4 hours and 40 minutes. Purified water (67.5 kg) was added at 20° C. over 2 hours to obtain a phase separation. The organic phase was diluted with EtOAc (61 kg) and washed with purified water (315 kg). The organic phase was concentrated under vacuum below 40° C. to approx. 150 l. Isopropanol (106 kg) was added and solution was concentrated again under vacuum to approx. 150 l. Isopropanol (248 kg) was added and the solution was heated to 48-52° C. Purified water (405 kg) was slowly added over approx. 2 hours obtaining a suspension that was stirred at 48-52° C. for 40 minutes then cooled to 18-22° C. over 3 hours and stirred at 20° C. for approx. 4 hours. Suspension was centrifugated and washed with a purified water/Isopropanol mixture (175 kg/106 kg). The wet solid was dried under vacuum in a static drier for about 8 hours affording Compound I (90.79 kg, yield 91.8%).

Example 12: Formation of Compound I-HCl Form 2

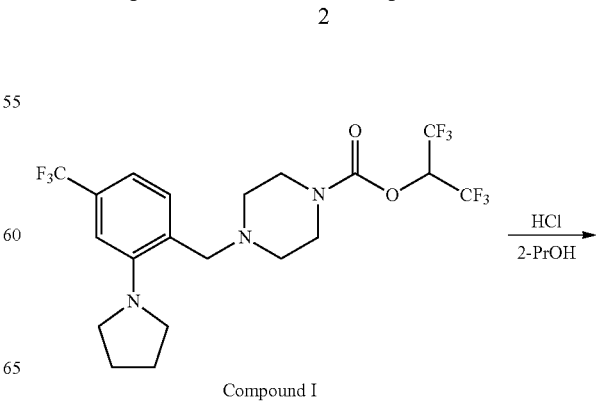

-continued

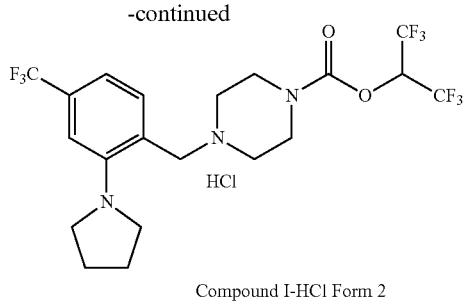

Compound I-HCl Form 2

Step d): Compound I (16.29 kg) was charged in a vessel followed by isopropanol (84.3 kg) and stirred at 38-40° C. for approx. 20 minutes. Solution was filtered in a second vessel and isopropanol (2.4 kg) was used as rinse from first to second vessel; temperature was maintained in the range 38-42° C. Approx. 6M HCl in isopropanol (1.1 kg) was added over approx. 15 minutes under stirring maintaining the temperature in the range 38-42° C. Seed (30 g) of Compound I-HCl form 2 was added followed by a second portion of 6M HCl in isopropanol (2.7 kg in approx. 15 minutes. The suspension was stirred at 38-42° C. for approx. 35 minutes. A third portion of 6M HCl in isopropanol (0.8 kg was added in approx. 15 minutes and the suspension was stirred for further approx. 70 minutes at 38-42° C., then cooled in approx. 60 minutes to 30° C., stirred for approx. 90 minutes, cooled to 20° C. in approx. 60 minutes and stirred at this temperature for up to 13 hours. Solid was isolated and washed with isopropanol (2×16 kg) and the wet solid was air dried at 35-40° C. for approx. 9 hours to end up with the desired product Compound I-HCl form 2 (15.96 kg, 91.4%). $^1$H-NMR (DMSO-$d_6$): δ(ppm) 1.90-1.93 (4H, t), 3.22-3.25 (8H, t), 3.82 (4H, bs), 4.49 (2H, bs), 6.60-6.67 (1H, m), 7.24-7.25 (2H, m), 7.92-7.94 (1H, d), 11.40 (1H, bs).

Example 13: Improved Formation of Compound I-HCl Form 2

Step d): Isopropanol (140 kg) was charged in a vessel at 20-25° C. then gaseous HCl (53.5 kg) was dosed for approx. 10 hours and then HCl/isopropanol solution was sampled for later use. Compound I (85 kg) was charged into a vessel followed by Isopropanol (400 kg), heated to about 38-42° C. and stirred till dissolution. The solution was then filtered in a second vessel (1487 liters, internal diameter: 1.2 m, diameter of impeller 0.72 m) followed by a rinse of isopropanol (67 kg). Previously prepared HCl/isopropanol solution (22.8 kg) was charged and the obtained mixture was heated to about 74-76° C. until complete dissolution was verified. Then, the solution was cooled to 65-68° C., and it was verified that it was still a solution. Subsequently, milled seeds of Compound I-HCl form 2 (1.7 kg) was added. The obtained suspension was stirred at approx. 77 RPM and at 65-68° C. for approx. 75 minutes, then cooled to 61-64° C. in approx. 2 hours and stirred approx. 2 hours at 61-64° C., then cooled to 51-53° C. in approx. 2 hours, then cooled to 36-38° C. in approx. 2 hours, then cooled to 18-20° C. in approx. 2 hours and finally stirred at 18-20° C. for further 6 hours. The wet solid was isolated and washed twice with isopropanol (2×67 kg each wash) obtaining 88.3 kg of wet product that was dried under vacuum at 35-40° C. for approx. 8 hours to end up with the desired product Compound I-HCl form 2 (84.41 kg, yield of 92.7%.

Example 14: Milling of Compound I-HCl Form 2

Starting from 84.11 kg of Compound I-HCl form 2 using an hammer mill (Nuova Guseo, sieve 0.5 mm, 3500 RPM) for around 30-60 min to provide 82.83 kg of milled Compound I-HCl form 2.

Example 15: Particle Size Distribution Determination

The analysis of particle size distribution of each batch was performed by an image analysis method on a Morphologi G3 Automated Particle Characterization System (Malvern PaNanalytical) with a sample Dispersion Unit SDU Glass Plate (180×110 mm); the instrument automatically process the collected data using the software Morphologi ver. 8.20 and provides a cumulative distribution curve and results in terms of d10, d50 and d90.

Table 1 shows the particle size distribution of Compound I-HCl form 2 made according to Example 13:

TABLE 1

| Particle size distribution of Compound I-HCl form 2 | |
|---|---|
| Compound | PSD result |
| Compound I-HCl form 2 | d10 53.5 μm |
| | d50 133.1 μm |
| | d90 201.7 μm |

The new process advantageously provided a reproducible and acceptable particle size of Compound I-HCl form 2. In order to optimize the PSD, the Compound I-HCl form 2 particles obtained from Example 13 was milled to provide smaller particles having superior properties with respect to tableting properties.

Table 2 shows the particle size distribution of Compound I-HCl form 2 made from Example 13 after milling.

TABLE 2

| Particle size distribution of Compound I-HCl form 2 after millnig | |
|---|---|
| Compound | PSD result |
| Compound I-HCI form 2 | d10 24 μm |
| | d50 67 μm |
| | d90 175 μm |

Example 17: X-Ray Powder Diffraction (XRPD)

XRPD analysis was carried out on a PANalytical X'pert pro, scanning the samples between 3 and 35° 2θ. The material was gently compressed into a multi well plate with Kapton or Mylar polymer film to support the sample. The multi well plate was then loaded into a PANalytical diffractometer running in transmission mode and analyzed, using the following experimental conditions:
Raw Data Origin: XRD measurement (*.XRDML)
Scan Axis: Gonio
Start Position [° 2θ]: 3.0066
End Position [° 2θ]: 34.9866
Step Size [° 2θ]: 0.0130
Scan Step Time [s]: 18.8700
Scan Type: Continuous
PSD Mode: Scanning
PSD Length [° 2θ]: 3.35

Offset [° 2θ]: 0.0000
Divergence Slit Type: Fixed
Divergence Slit Size [°]: 1.0000
Measurement Temperature [° C.]: 25.00
Anode Material: Cu
K-Alpha1 [Å]: 1.54060
K-Alpha2 [Å]: 1.54443
K-Beta [æ]: 1.39225
K-A2/K-A1 Ratio: 0.50000
Generator Settings: 40 mA, 40 kV
Goniometer Radius [mm]: 240.00
Dist. Focus-Diverg. Slit [mm]: 91.00
Incident Beam Monochromator: No
Spinning: No

The invention claimed is:

1. A process for the manufacture of 1,1,1,3,3,3-hexafluoropropan-2-yl 4-(2-(pyrrolidin-1-yl)-4-(trifluoromethyl)benzyl)piperazine-1-carboxylate comprising the steps of:
   a) reacting tert-butyl piperazine-1-carboxylate with hexafluoropropan-2-ol in the presence of an acyl transfer agent to form 1-(tert-butyl) 4-(1,1,1,3,3,3-hexafluoropropan-2-yl) piperazine-1,4-dicarboxylate, wherein step a) is carried out in a first solvent;
   b) reacting 1-(tert-butyl) 4-(1,1,1,3,3,3-hexafluoropropan-2-yl) piperazine-1,4-dicarboxylate obtained in step a) with a strong acid to form 1,1,1,3,3,3-hexafluoropropan-2-yl piperazine-1-carboxylate, or a pharmaceutically acceptable salt thereof, wherein step b) is optionally carried out in a second solvent;
   c) reacting 1,1,1,3,3,3-hexafluoropropan-2-yl piperazine-1-carboxylate, or a pharmaceutically acceptable salt thereof obtained in step b) with 2-(pyrrolidin-1-yl)-4-(trifluoromethyl)benzaldehyde in the presence of a reducing agent and an organic base to form a reaction mixture comprising 1,1,1,3,3,3-hexafluoropropan-2-yl 4-(2-(pyrrolidin-1-yl)-4-(trifluoromethyl)benzyl)piperazine-1-carboxylate, wherein the reaction in step c) is carried out in a third solvent; and further comprises steps (iii)-(v):
      (iii) adding water to the reaction mixture comprising 1,1,1,3,3,3-hexafluoropropan-2-yl 4-(2-(pyrrolidin-1-yl)-4-(trifluoromethyl)benzyl)piperazine-1-carboxylate to form a phase separation having an organic phase comprising 1,1,1,3,3,3-hexafluoropropan-2-yl 4-(2-(pyrrolidin-1-yl)-4-(trifluoromethyl)benzyl)piperazine-1-carboxylate, followed by diluting the organic phase with the third solvent;
      (iv) adding an $C_1$-$C_4$ alcohol to the organic phase comprising 1,1,1,3,3,3-hexafluoropropan-2-yl 4-(2-(pyrrolidin-1-yl)-4-(trifluoromethyl)benzyl)piperazine-1-carboxylate to provide a solution comprising 1,1,1,3,3,3-hexafluoropropan-2-yl 4-(2-(pyrrolidin-1-yl)-4-(trifluoromethyl)benzyl)piperazine-1-carboxylate, optionally concentrating the solution; and
      (v) adding water to the solution comprising 1,1,1,3,3,3-hexafluoropropan-2-yl 4-(2-(pyrrolidin-1-yl)-4-(trifluoromethyl)benzyl)piperazine-1-carboxylate to form a suspension comprising 1,1,1,3,3,3-hexafluoropropan-2-yl 4-(2-(pyrrolidin-1-yl)-4-(trifluoromethyl)benzyl)piperazine-1-carboxylate.

2. The process according to claim 1, wherein step a) is carried out under pressure of 2 bar to 6 bar.

3. The process according to claim 1, wherein the ingredients in step a) are added in the consecutive order of the acyl transfer agent, the first solvent, tert-butyl piperazine-1-carboxylate, and hexafluoropropan-2-ol as the last ingredient.

4. The process according to claim 1, wherein the strong acid in step b) is HCl; and wherein the step b) is carried out in a second solvent.

5. The process according to claim 4, wherein the second solvent is selected from the group consisting of toluene, isopropyl acetate, dichloromethane, acetonitrile, ethers and esters.

6. The process according to claim 1, wherein the third solvent in step c) is ethyl acetate.

7. The process according to claim 1, wherein step c) comprises the steps of:
   i) providing a mixture comprising 1,1,1,3,3,3-hexafluoropropan-2-yl piperazine-1-carboxylate, or a pharmaceutically acceptable salt thereof obtained in step b), 2-(pyrrolidin-1-yl)-4-(trifluoromethyl)benzaldehyde, the organic base, and the third solvent;
   ii) adding the reducing agent to the mixture obtained from step i) to provide a reaction mixture comprising 1,1,1,3,3,3-hexafluoropropan-2-yl 4-(2-(pyrrolidin-1-yl)-4-(trifluoromethyl)benzyl)piperazine-1-carboxylate.

8. The process according to claim 1, wherein step c) further comprises the step of:
   vi) isolating 1,1,1,3,3,3-hexafluoropropan-2-yl 4-(2-(pyrrolidin-1-yl)-4-(trifluoromethyl)benzyl)piperazine-1-carboxylate from the suspension comprising 1,1,1,3,3,3-hexafluoropropan-2-yl 4-(2-(pyrrolidin-1-yl)-4-(trifluoromethyl)benzyl)piperazine-1-carboxylate.

9. The process according to claim 1, wherein 2-(pyrrolidin-1-yl)-4-(trifluoromethyl)benzaldehyde is obtained in step c0) prior to step c), wherein step c0) comprises the step of reacting 2-fluoro-4-(trifluoromethyl)benzaldehyde with pyrrolidine in the presence of an inorganic base to form 2-(pyrrolidine-1-yl)-4-(trifluoromethyl)benzaldehyde, wherein the reaction in step c0) is carried out in a fourth solvent.

10. The process according to claim 9, wherein the inorganic base and the fourth solvent in step c0) are $Na_2CO_3$ and ethyl acetate, respectively.

11. The process according to claim 10, wherein step c0) further comprises adding around 1-2% w/w of water to the mixture comprising ethyl acetate and 2-(pyrrolidine-1-yl)-4-(trifluoromethyl)benzaldehyde.

12. A process for the manufacture of crystalline 1,1,1,3,3,3-hexafluoropropan-2-yl 4-(2-(pyrrolidin-1-yl)-4-(trifluoromethyl)benzyl)piperazine-1-carboxylate mono-hydrochloride salt form 2 comprising the steps of:
   a) reacting tert-butyl piperazine-1-carboxylate with hexafluoropropan-2-ol in the presence of an acyl transfer agent to form 1-(tert-butyl) 4-(1,1,1,3,3,3-hexafluoropropan-2-yl) piperazine-1,4-dicarboxylate, wherein step a) is carried out in a first solvent;
   b) reacting 1-(tert-butyl) 4-(1,1,1,3,3,3-hexafluoropropan-2-yl) piperazine-1,4-dicarboxylate obtained in step a) with a strong acid to form 1,1,1,3,3,3-hexafluoropropan-2-yl piperazine-1-carboxylate, or a pharmaceutically acceptable salt thereof, wherein step b) is optionally carried out in a second solvent;
   c) reacting 1,1,1,3,3,3-hexafluoropropan-2-yl piperazine-1-carboxylate, or a pharmaceutically acceptable salt thereof obtained in step b) with 2-(pyrrolidin-1-yl)-4-(trifluoromethyl)benzaldehyde in the presence of a reducing agent and an organic base to form a reaction mixture comprising 1,1,1,3,3,3-hexafluoropropan-2-yl 4-(2-(pyrrolidin-1-yl)-4-(trifluoromethyl)benzyl)piperazine-1-carboxylate, wherein the reaction in step c) is carried out in a third solvent;

d) converting 1,1,1,3,3,3-hexafluoropropan-2-yl 4-(2-(pyrrolidin-1-yl)-4-(trifluoromethyl)benzyl)piperazine-1-carboxylate to crystalline 1,1,1,3,3,3-hexafluoropropan-2-yl 4-(2-(pyrrolidin-1-yl)-4-(trifluoromethyl)benzyl)piperazine-1-carboxylate mono-hydrochloride salt form 2;

further comprising the steps of:

d1) dissolving 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof in a fifth solvent at a temperature of 38-70° C., optionally under stirring;

d2) converting the 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof into 1,1,1,3,3,3-hexafluoropropan-2-yl 4-(2-(pyrrolidin-1-yl)-4-(trifluoromethyl)benzyl)piperazine-1-carboxylate mono-hydrochloride salt by addition of HCl, optionally under stirring at a temperature of 70-76° C.;

d3) optionally filtering the solution obtained in step d2)

d4) cooling the solution to 63-69° C., and adding seed crystals of 1,1,1,3,3,3-hexafluoropropan-2-yl 4-(2-(pyrrolidin-1-yl)-4-(trifluoromethyl)benzyl)piperazine-1-carboxylate mono-hydrochloride salt form 2;

d5) optionally, stirring the suspension for at least 1 hour;

d6) cooling the suspension from 63-69° C. to a temperature of 10-40° C. during a period between 12-20 hours under stirring.

13. The process according to claim 12, wherein the process further comprises a step of milling crystalline 1,1,1,3,3,3-hexafluoropropan-2-yl 4-(2-(pyrrolidin-1-yl)-4-(trifluoromethyl)benzyl)piperazine-1-carboxylate mono-hydrochloride salt form 2.

14. The process according to claim 13, wherein the obtained crystalline 1,1,1,3,3,3-hexafluoropropan-2-yl 4-(2-(pyrrolidin-1-yl)-4-(trifluoromethyl)benzyl)piperazine-1-carboxylate mono-hydrochloride salt form 2 is characterized by having a d10 particle size of 10-30 μm; a d90 particle size below 200 μm, optionally a d50 particle size ranging of 60-80 μm.

15. The process according to claim 12, wherein the obtained crystalline 1,1,1,3,3,3-hexafluoropropan-2-yl 4-(2-(pyrrolidin-1-yl)-4-(trifluoromethyl)benzyl)piperazine-1-carboxylate mono-hydrochloride salt form 2 is formulated into a tablet together with at least one excipient.

16. The process according to claim 12, wherein the obtained crystalline 1,1,1,3,3,3-hexafluoropropan-2-yl 4-(2-(pyrrolidin-1-yl)-4-(trifluoromethyl)benzyl)piperazine-1-carboxylate mono-hydrochloride salt form 2 is characterized by having an X-ray powder diffraction (XRPD) pattern with characteristic peaks at 8.6° 2-Theta, 14.3° 2-Theta, 15.6° 2-Theta, 19.0° 2-Theta, 19.8° 2-Theta, and 20.7° 2-Theta.

\* \* \* \* \*

UNITED STATES PATENT AND TRADEMARK OFFICE
CERTIFICATE OF CORRECTION

| | |
|---|---|
| PATENT NO. | : 11,702,393 B2 |
| APPLICATION NO. | : 17/234660 |
| DATED | : July 18, 2023 |
| INVENTOR(S) | : Giuseppe Guercio |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 128 days.

Signed and Sealed this
Twelfth Day of November, 2024

Katherine Kelly Vidal
*Director of the United States Patent and Trademark Office*